US010335521B2

(12) United States Patent
Pinto et al.

(10) Patent No.: US 10,335,521 B2
(45) Date of Patent: Jul. 2, 2019

(54) REDUCED PRESSURE THERAPY DEVICES

(75) Inventors: Moshe Pinto, Mountain View, CA (US); Dean Hu, San Leandro, CA (US); Kenton Fong, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 343 days.

(21) Appl. No.: 13/221,734

(22) Filed: Aug. 30, 2011

(65) Prior Publication Data

US 2011/0313377 A1 Dec. 22, 2011

Related U.S. Application Data

(63) Continuation of application No. 12/234,530, filed on Sep. 19, 2008, now Pat. No. 8,007,491, which is a (Continued)

(51) Int. Cl.
*A61M 1/00* (2006.01)
*A61F 13/00* (2006.01)
(Continued)

(52) U.S. Cl.
CPC ..... *A61M 1/0088* (2013.01); *A61F 13/00029* (2013.01); *A61F 13/00068* (2013.01);
(Continued)

(58) Field of Classification Search
CPC .......................... A61F 13/00068; A61F 13/069
(Continued)

(56) References Cited

U.S. PATENT DOCUMENTS

| 406,330 A | 7/1889 | Austin |
| 418,469 A | 12/1889 | McKinley |

(Continued)

FOREIGN PATENT DOCUMENTS

| AU | 550575 B2 | 3/1986 |
| AU | 745271 B2 | 3/2002 |

(Continued)

OTHER PUBLICATIONS

US 7,186,244 B1, 03/2007, Hunt et al. (withdrawn)
(Continued)

*Primary Examiner* — Andrew J Mensh

(57) ABSTRACT

Described generally herein are tissue therapy devices, which may comprise a sealant layer and a suction apparatus. The sealant layer functions so as to create a sealed enclosure between it and the surface of a patient by forming, preferably, an airtight seal around an area of tissue that requires negative pressure therapy. The tissue therapy device may comprise a suction apparatus. The suction apparatus is typically in fluid communication with the sealant layer and functions so as to reduce the amount of pressure present underneath the sealant layer. The reduced pressure is self-created by the suction apparatus. Together the sealant layer and the suction apparatus preferably create a closed reduced pressure therapy system. Preferably, the pressure under the sealant layer is reduced by expanding the volume of the enclosure space and thereby decreasing the density of the air molecules under the sealant layer.

8 Claims, 13 Drawing Sheets

Related U.S. Application Data continuation of application No. 12/047,739, filed on Mar. 13, 2008, now Pat. No. 10,117,977.

(60) Provisional application No. 60/973,086, filed on Sep. 17, 2007, provisional application No. 60/906,721, filed on Mar. 14, 2007.

(51) Int. Cl.
    *A61M 27/00*     (2006.01)
    *A61F 13/06*     (2006.01)

(52) U.S. Cl.
    CPC ........... *A61M 1/007* (2014.02); *A61F 13/069* (2013.01); *A61F 2013/0054* (2013.01); *A61F 2013/00174* (2013.01); *A61F 2013/00412* (2013.01); *A61F 2013/00519* (2013.01); *A61F 2013/00536* (2013.01); *A61M 1/0062* (2013.01); *A61M 1/0084* (2013.01)

(58) Field of Classification Search
    USPC .................................................. 604/540, 543
    See application file for complete search history.

(56) References Cited

U.S. PATENT DOCUMENTS

| | | | |
|---|---|---|---|
| 617,936 | A | 1/1899 | Nicolas |
| 1,355,846 | A | 10/1920 | Rannells |
| 2,198,666 | A | 4/1940 | Gruskin |
| 2,306,107 | A | 12/1942 | Henderson |
| 2,472,116 | A | 6/1949 | Maynes |
| 2,523,850 | A * | 9/1950 | Steinberg ............... 604/209 |
| 2,547,758 | A | 4/1951 | Keeling |
| 2,632,443 | A | 3/1953 | Lesher |
| 2,660,342 | A | 11/1953 | Ruf |
| 2,682,873 | A | 7/1954 | Evans et al. |
| 2,863,452 | A | 12/1958 | Ogle, Sr. |
| 2,910,763 | A | 11/1959 | Lauterbach |
| 2,969,057 | A | 1/1961 | Simmons |
| 3,066,672 | A | 12/1962 | Crosby, Jr. et al. |
| 3,073,309 | A | 1/1963 | Mosier |
| 3,334,628 | A | 8/1967 | Saemann et al. |
| 3,367,332 | A | 2/1968 | Groves |
| 3,401,522 | A | 9/1968 | Hann et al. |
| 3,520,300 | A | 7/1970 | Flower, Jr. |
| 3,568,675 | A | 3/1971 | Harvey |
| 3,583,399 | A | 6/1971 | Ritsky |
| 3,628,325 | A | 12/1971 | Morita |
| 3,648,692 | A | 3/1972 | Wheeler |
| 3,680,560 | A | 8/1972 | Pannier, Jr. et al. |
| 3,682,180 | A | 8/1972 | McFarlane |
| 3,750,393 | A | 8/1973 | Minto et al. |
| 3,779,243 | A | 12/1973 | Tussey et al. |
| 3,809,086 | A | 5/1974 | Schachet et al. |
| 3,809,087 | A | 5/1974 | Lewis, Jr. |
| 3,826,254 | A | 7/1974 | Mellor |
| 3,833,030 | A | 9/1974 | Waldbauer, Jr. et al. |
| 3,841,331 | A | 10/1974 | Wilder et al. |
| 3,864,766 | A | 2/1975 | Prete, Jr. |
| 3,958,570 | A | 5/1976 | Vogelman et al. |
| 3,982,546 | A | 9/1976 | Friend |
| 4,041,934 | A | 8/1977 | Genese |
| 4,067,330 | A | 1/1978 | Roache |
| 4,080,970 | A | 3/1978 | Miller |
| 4,096,853 | A | 6/1978 | Weigand |
| 4,124,116 | A * | 11/1978 | McCabe, Jr. ............... 96/108 |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,278,089 | A | 7/1981 | Huck et al. |
| 4,284,079 | A | 8/1981 | Adair |
| 4,287,819 | A | 9/1981 | Emerit |
| 4,297,995 | A | 11/1981 | Golub |
| 4,333,456 | A | 6/1982 | Webb |
| 4,333,458 | A | 6/1982 | Margulies et al. |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,404,924 | A | 9/1983 | Goldberg et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,484,919 | A | 11/1984 | Sohn et al. |
| 4,525,166 | A | 6/1985 | Leclerc |
| 4,525,167 | A | 6/1985 | Goldberg et al. |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,549,554 | A | 10/1985 | Markham |
| 4,551,139 | A | 11/1985 | Plaas et al. |
| 4,569,348 | A | 2/1986 | Hasslinger |
| 4,569,674 | A | 2/1986 | Phillips et al. |
| 4,578,060 | A | 3/1986 | Huck et al. |
| 4,605,399 | A | 8/1986 | Weston et al. |
| 4,608,041 | A | 8/1986 | Nielsen |
| 4,640,688 | A | 2/1987 | Hauser |
| 4,648,870 | A | 3/1987 | Goldberg et al. |
| 4,655,754 | A | 4/1987 | Richmond et al. |
| 4,664,128 | A | 5/1987 | Lee |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,747,960 | A * | 5/1988 | Freeman et al. ............... 210/689 |
| 4,758,220 | A | 7/1988 | Sundblom et al. |
| 4,758,232 | A | 7/1988 | Chak |
| 4,787,888 | A | 11/1988 | Fox |
| 4,810,249 | A * | 3/1989 | Haber ............... A61M 5/31555 222/390 |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,867,748 | A | 9/1989 | Samuelsen |
| 4,872,450 | A | 10/1989 | Austad |
| 4,878,901 | A | 11/1989 | Sachse |
| 4,882,337 | A | 11/1989 | Sweet et al. |
| 4,882,377 | A | 11/1989 | Sweet et al. |
| 4,889,250 | A | 12/1989 | Beyer |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,002,528 | A * | 3/1991 | Palestrant ........... A61M 3/0241 604/246 |
| 5,018,516 | A | 5/1991 | Gilman |
| 5,037,397 | A | 8/1991 | Kalt et al. |
| 5,071,409 | A | 12/1991 | Rosenberg |
| 5,073,172 | A | 12/1991 | Fell |
| 5,086,170 | A | 2/1992 | Luheshi et al. |
| 5,092,858 | A | 3/1992 | Benson et al. |
| 5,100,396 | A | 3/1992 | Zamierowski |
| 5,107,859 | A * | 4/1992 | Alcorn et al. ............... 128/853 |
| 5,116,310 | A | 5/1992 | Seder et al. |
| 5,116,610 | A | 5/1992 | Broaddus |
| 5,133,821 | A | 7/1992 | Jensen |
| 5,134,994 | A | 8/1992 | Say |
| 5,149,331 | A | 9/1992 | Ferdman et al. |
| 5,154,697 | A | 10/1992 | Loori |
| 5,157,808 | A | 10/1992 | Sterner, Jr. |

(56) References Cited

U.S. PATENT DOCUMENTS

| | | | |
|---|---|---|---|
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,263,922 A | 11/1993 | Sova et al. | |
| 5,266,476 A | 11/1993 | Sussman et al. | |
| 5,278,100 A | 1/1994 | Doan et al. | |
| 5,279,550 A | 1/1994 | Habib et al. | |
| 5,284,621 A | 2/1994 | Kaufman | |
| 5,298,015 A | 3/1994 | Komatsuzaki | |
| 5,339,830 A * | 8/1994 | Blake, III | G01N 33/4905 422/73 |
| 5,342,376 A | 8/1994 | Ruff | |
| 5,344,415 A | 9/1994 | DeBusk et al. | |
| 5,356,372 A | 10/1994 | Donovan et al. | |
| 5,358,494 A | 10/1994 | Svedman | |
| 5,380,295 A * | 1/1995 | Vacca | 604/187 |
| 5,395,345 A | 3/1995 | Gross | |
| 5,437,622 A | 8/1995 | Carion | |
| 5,437,651 A | 8/1995 | Todd et al. | |
| 5,527,293 A | 6/1996 | Zamierowski | |
| 5,531,999 A * | 7/1996 | Cartmell et al. | 424/445 |
| 5,549,584 A | 8/1996 | Gross | |
| 5,556,375 A | 9/1996 | Ewall | |
| 5,584,801 A | 12/1996 | Kuroyanagi et al. | |
| 5,607,388 A | 3/1997 | Ewall | |
| 5,636,643 A | 6/1997 | Argenta et al. | |
| 5,645,081 A | 7/1997 | Argenta et al. | |
| H001687 H | 10/1997 | Roe et al. | |
| 5,701,917 A | 12/1997 | Khouri | |
| 5,704,905 A | 1/1998 | Jensen et al. | |
| 5,711,969 A * | 1/1998 | Patel et al. | 424/551 |
| 5,845,641 A * | 12/1998 | Pinney et al. | 128/849 |
| 5,961,497 A | 10/1999 | Larkin | |
| 5,970,979 A * | 10/1999 | Christofel et al. | 128/849 |
| 6,071,267 A | 6/2000 | Zamierowski | |
| 6,135,116 A | 10/2000 | Vogel et al. | |
| 6,142,982 A | 11/2000 | Hunt et al. | |
| 6,174,306 B1 | 1/2001 | Fleischmann | |
| 6,211,426 B1 | 4/2001 | Abrams | |
| 6,235,964 B1 | 5/2001 | Kadash et al. | |
| 6,241,747 B1 | 6/2001 | Ruff | |
| 6,258,995 B1 | 7/2001 | Gilding et al. | |
| 6,261,276 B1 | 7/2001 | Reitsma | |
| 6,266,859 B1 | 7/2001 | Hernandez | |
| 6,287,316 B1 | 9/2001 | Agarwal et al. | |
| 6,345,623 B1 | 2/2002 | Heaton et al. | |
| 6,368,305 B1 | 4/2002 | Dutton | |
| 6,387,082 B1 | 5/2002 | Freeman | |
| 6,458,109 B1 | 10/2002 | Henley et al. | |
| 6,461,467 B2 | 10/2002 | Blatchford et al. | |
| 6,467,432 B1 | 10/2002 | Lewis et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| 6,752,794 B2 | 6/2004 | Lockwood et al. | |
| 6,755,807 B2 | 6/2004 | Risk, Jr. et al. | |
| 6,800,074 B2 | 10/2004 | Henley et al. | |
| 6,814,079 B2 | 11/2004 | Heaton et al. | |
| 6,825,246 B1 | 11/2004 | Fattman | |
| 6,855,135 B2 | 2/2005 | Lockwood et al. | |
| 6,913,573 B1 | 7/2005 | Viscomi et al. | |
| 6,979,324 B2 | 12/2005 | Bybordi et al. | |
| 6,986,234 B2 | 1/2006 | Liedtke | |
| 7,070,584 B2 | 7/2006 | Johnson et al. | |
| 7,117,869 B2 | 10/2006 | Heaton et al. | |
| 7,198,046 B1 | 4/2007 | Argenta et al. | |
| 7,216,651 B2 | 5/2007 | Argenta et al. | |
| 7,273,054 B2 | 9/2007 | Heaton et al. | |
| 7,316,672 B1 | 1/2008 | Hunt et al. | |
| 7,341,574 B2 | 3/2008 | Schreijag | |
| 7,448,653 B2 | 11/2008 | Jensen et al. | |
| 7,461,158 B2 | 12/2008 | Rider et al. | |
| 7,485,112 B2 | 2/2009 | Karpowicz et al. | |
| 7,520,872 B2 | 4/2009 | Biggie et al. | |
| 7,569,745 B2 | 8/2009 | Sticklen et al. | |
| 7,597,690 B2 | 10/2009 | Tanio et al. | |
| D607,112 S | 12/2009 | Rogers et al. | |
| D618,337 S | 6/2010 | Pratt et al. | |
| 7,763,000 B2 | 7/2010 | Risk, Jr. et al. | |
| 7,771,377 B2 * | 8/2010 | Stapf et al. | 602/3 |
| 7,779,625 B2 | 8/2010 | Joshi et al. | |
| D624,177 S | 9/2010 | Pratt et al. | |
| 7,794,438 B2 | 9/2010 | Henley et al. | |
| 7,837,673 B2 | 11/2010 | Vogel | |
| 7,863,495 B2 * | 1/2011 | Aali | 602/42 |
| 7,875,761 B2 | 1/2011 | Budig et al. | |
| 7,880,050 B2 | 2/2011 | Robinson et al. | |
| 7,926,856 B2 | 4/2011 | Smutney et al. | |
| 7,928,279 B2 | 4/2011 | Rosenberg | |
| 7,928,281 B2 * | 4/2011 | Augustine | 602/48 |
| 7,942,866 B2 | 5/2011 | Radl et al. | |
| 7,959,624 B2 | 6/2011 | Riesinger | |
| 8,007,257 B2 | 8/2011 | Heaton et al. | |
| 8,007,491 B2 | 8/2011 | Pinto et al. | |
| 8,128,607 B2 | 3/2012 | Hu et al. | |
| 8,148,595 B2 | 4/2012 | Robinson et al. | |
| 8,162,908 B2 | 4/2012 | Hu et al. | |
| 8,177,764 B2 | 5/2012 | Hu et al. | |
| 8,287,507 B2 | 10/2012 | Heaton et al. | |
| 8,308,705 B2 * | 11/2012 | Lin et al. | 604/327 |
| 8,337,474 B2 | 12/2012 | Hu et al. | |
| 8,361,043 B2 | 1/2013 | Hu et al. | |
| 8,409,156 B2 | 4/2013 | Kazala, Jr. et al. | |
| 8,409,157 B2 | 4/2013 | Haggstrom et al. | |
| 8,409,160 B2 | 4/2013 | Locke et al. | |
| 8,535,283 B2 | 9/2013 | Heaton et al. | |
| 8,641,692 B2 | 2/2014 | Tout et al. | |
| 8,679,079 B2 | 3/2014 | Heaton et al. | |
| 8,864,748 B2 | 10/2014 | Coulthard et al. | |
| 2001/0031943 A1 | 10/2001 | Urie | |
| 2001/0043943 A1 | 11/2001 | Coffey | |
| 2002/0026133 A1 | 2/2002 | Augustine et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0150720 A1 | 10/2002 | Howard et al. | |
| 2002/0173808 A1 | 11/2002 | Houser et al. | |
| 2002/0183702 A1 | 12/2002 | Henley et al. | |
| 2002/0198503 A1 | 12/2002 | Risk, Jr. et al. | |
| 2003/0040718 A1 * | 2/2003 | Kust | A61B 17/8822 604/224 |
| 2003/0050594 A1 | 3/2003 | Zamierowski | |
| 2003/0088201 A1 * | 5/2003 | Darcey | 602/44 |
| 2003/0120194 A1 * | 6/2003 | Stapf | 602/48 |
| 2003/0190339 A1 | 10/2003 | Skover et al. | |
| 2004/0249353 A1 | 12/2004 | Risks, Jr. et al. | |
| 2004/0261642 A1 | 12/2004 | Hess | |
| 2005/0020980 A1 * | 1/2005 | Inoue | A61M 5/14244 604/152 |
| 2005/0101940 A1 | 5/2005 | Radl et al. | |
| 2005/0192544 A1 | 9/2005 | Wolbring et al. | |
| 2005/0222527 A1 * | 10/2005 | Miller et al. | 602/1 |
| 2005/0261642 A1 | 11/2005 | Weston | |
| 2005/0267433 A1 | 12/2005 | Tanio et al. | |
| 2006/0253090 A1 | 11/2006 | Bradley et al. | |
| 2006/0282028 A1 | 12/2006 | Howard et al. | |
| 2007/0027414 A1 | 2/2007 | Hoffman et al. | |
| 2007/0066946 A1 | 3/2007 | Haggstrom et al. | |
| 2007/0066948 A1 | 3/2007 | Erdman | |
| 2007/0219512 A1 | 9/2007 | Heaton et al. | |
| 2007/0219532 A1 | 9/2007 | Karpowicz et al. | |
| 2007/0233022 A1 | 10/2007 | Henley et al. | |
| 2007/0265586 A1 | 11/2007 | Joshi et al. | |
| 2008/0004559 A1 | 1/2008 | Riesinger | |
| 2008/0009812 A1 * | 1/2008 | Riesinger | 604/305 |
| 2008/0033330 A1 | 2/2008 | Moore | |
| 2008/0063615 A1 | 3/2008 | MacDonald et al. | |
| 2008/0082059 A1 | 4/2008 | Fink et al. | |

(56) References Cited

U.S. PATENT DOCUMENTS

| | | |
|---|---|---|
| 2008/0086214 A1 | 4/2008 | Hardin et al. |
| 2008/0108977 A1 | 5/2008 | Heaton et al. |
| 2008/0200906 A1 | 8/2008 | Sanders et al. |
| 2008/0234641 A1 | 9/2008 | Locke et al. |
| 2008/0294147 A1 | 11/2008 | Radl et al. |
| 2008/0306448 A1 | 12/2008 | Lee |
| 2008/0306456 A1 | 12/2008 | Riesinger |
| 2009/0012482 A1 | 1/2009 | Pinto et al. |
| 2009/0076467 A1 | 3/2009 | Pinto et al. |
| 2009/0187130 A1 | 7/2009 | Asmus et al. |
| 2009/0221977 A1 | 9/2009 | Blott et al. |
| 2009/0240218 A1 | 9/2009 | Braga et al. |
| 2009/0254066 A1 | 10/2009 | Heaton et al. |
| 2010/0030166 A1 | 2/2010 | Tout et al. |
| 2010/0036333 A1 | 2/2010 | Schenk, III et al. |
| 2010/0042021 A1 | 2/2010 | Hu et al. |
| 2010/0042059 A1 | 2/2010 | Pratt et al. |
| 2010/0100063 A1 | 4/2010 | Joshi et al. |
| 2010/0137775 A1 | 6/2010 | Hu et al. |
| 2010/0145289 A1 | 6/2010 | Lina et al. |
| 2010/0160879 A1 | 6/2010 | Weston |
| 2010/0160901 A1 | 6/2010 | Hu et al. |
| 2010/0168719 A1 | 7/2010 | Chen |
| 2010/0174250 A1 | 7/2010 | Hu et al. |
| 2010/0179493 A1 | 7/2010 | Heagle et al. |
| 2010/0198174 A1 | 8/2010 | Hu et al. |
| 2010/0228205 A1 | 9/2010 | Hu et al. |
| 2010/0262090 A1 | 10/2010 | Riesinger |
| 2010/0262094 A1 | 10/2010 | Walton et al. |
| 2010/0324510 A1 | 12/2010 | Andresen et al. |
| 2011/0106030 A1 | 5/2011 | Scholz |
| 2011/0130691 A1 | 6/2011 | Hu et al. |
| 2011/0137270 A1 | 6/2011 | Hu et al. |
| 2012/0016325 A1 | 1/2012 | Pinto et al. |
| 2012/0078207 A1 | 3/2012 | Hu et al. |
| 2013/0006204 A1 | 1/2013 | Hu et al. |
| 2013/0090615 A1 | 4/2013 | Jaeb et al. |
| 2013/0096536 A1 | 4/2013 | Kazala, Jr. et al. |
| 2013/0144231 A1 | 6/2013 | Hu et al. |
| 2014/0100539 A1 | 4/2014 | Coulthard et al. |
| 2014/0200535 A1 | 7/2014 | Locke et al. |
| 2015/0018784 A1 | 1/2015 | Coulthard et al. |
| 2015/0094673 A1 | 4/2015 | Pratt et al. |
| 2015/0094674 A1 | 4/2015 | Pratt et al. |

FOREIGN PATENT DOCUMENTS

| | | |
|---|---|---|
| AU | 755496 B2 | 12/2002 |
| CA | 2005436 A1 | 6/1990 |
| CN | 1438904 A | 8/2003 |
| CN | 2851641 Y | 12/2006 |
| DE | 26 40 413 A1 | 3/1978 |
| DE | 43 06 478 A1 | 9/1994 |
| DE | 29 504 378 U1 | 9/1995 |
| DE | 19517699 A1 | 11/1996 |
| DE | 202004017052 U1 | 6/2005 |
| DE | 20 2005 019 670 U1 | 6/2006 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0360329 A1 | 3/1990 |
| EP | 1018967 A1 | 7/2000 |
| EP | 2098257 A1 | 9/2009 |
| FR | 1163907 A | 10/1958 |
| GB | 692578 A | 6/1953 |
| GB | 2 195 255 A | 4/1988 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 306 107 A | 4/1997 |
| GB | 2 329 127 A | 3/1999 |
| GB | 2 333 965 A | 8/1999 |
| GB | 2 431 351 A | 4/2007 |
| JP | 55-68370 A | 5/1980 |
| JP | 59-177055 A | 10/1984 |
| JP | 4-506760 A | 11/1992 |
| JP | 11-504833 A | 5/1999 |
| JP | 2003-284770 A | 10/2003 |
| JP | 2003-532504 A | 11/2003 |
| JP | 2007-534403 A | 11/2007 |
| JP | 4129536 B2 | 8/2008 |
| JP | 2010-506615 A | 3/2010 |
| SG | 71559 | 4/2002 |
| WO | 80/02182 A1 | 10/1980 |
| WO | WO-80/02182 A1 | 10/1980 |
| WO | 87/04626 A1 | 8/1987 |
| WO | 90/010424 A1 | 9/1990 |
| WO | 1991/000718 A1 | 1/1991 |
| WO | 93/009727 A1 | 5/1993 |
| WO | 94/020041 A1 | 9/1994 |
| WO | 96/05873 A1 | 2/1996 |
| WO | 1996/035401 A1 | 11/1996 |
| WO | 97/18007 A1 | 5/1997 |
| WO | 99/13793 A1 | 3/1999 |
| WO | 2001/085248 A1 | 11/2001 |
| WO | 2003/070135 A2 | 8/2003 |
| WO | 2004/037334 A1 | 5/2004 |
| WO | 2005/051461 A1 | 6/2005 |
| WO | 2005/105179 A1 | 11/2005 |
| WO | WO-2006/005939 A1 | 1/2006 |
| WO | WO 2006048240 A1 * | 5/2006 |
| WO | WO-2007/030601 A2 | 3/2007 |
| WO | WO-2007/030601 A3 | 3/2007 |
| WO | WO-2007/067685 A2 | 6/2007 |
| WO | WO-2007/067685 A3 | 6/2007 |
| WO | 2007/123451 A1 | 11/2007 |
| WO | 2008/048527 A2 | 4/2008 |
| WO | WO-2008/100446 A2 | 8/2008 |
| WO | WO-2008/100446 A3 | 8/2008 |
| WO | WO-2008/112304 A1 | 9/2008 |
| WO | 2009/002260 A1 | 12/2008 |
| WO | WO-2009/089016 A1 | 7/2009 |
| WO | WO-2009/103031 A1 | 8/2009 |
| WO | WO-2010/068502 A1 | 6/2010 |
| WO | 2010/080907 A1 | 7/2010 |
| WO | WO-2010/102146 A1 | 9/2010 |
| WO | 2013/078214 A1 | 5/2013 |

OTHER PUBLICATIONS

Office Action received for Chinese Patent Application No. 200980112984.X, dated Dec. 4, 2012, 13 pages (5 pages of English Translation and 8 pages of Official Copy).

Office Action received for Chinese Patent Application No. 200980112984.X, dated Aug. 16, 2013, 11 pages (4 pages of English Translation and 7 pages of Office Action).

Office Action received for Japanese Patent Application No. 2012-229673, dated Sep. 17, 2013, 5 pages (3 pages of English Translation and 2 pages of Office Action).

Extended European Search Report received for European Patent Application No. 09832371.0, dated Feb. 26, 2013, 8 pages.

Office Action received for European Patent Application No. 09709714.1, dated Jan. 26, 2011, 4 pages.

Office Action received for European Patent Application No. 09709714.1, dated Mar. 20, 2013, 4 pages.

Non Final Office Action received for U.S. Appl. No. 12/646,856 dated Feb. 26, 2013, 18 pages.

Non Final Office Action received for U.S. Appl. No. 12/626,426 dated Mar. 1, 2013, 9 pages.

Final Office Action received for U.S. Appl. No. 12/717,838 dated Apr. 11, 2013, 15 pages.

Anonymous. (Feb. 10, 2000). "Drain and Suture Line Care for Wounds," *The Cleveland Clinic Foundation*, located at <http://www.clevelandclinic.org/health/health-info/docs/2200/2205.asp?i . . . >, last visited Oct. 15, 2007, four pages.

Bagautdinov, N.A. (1986). "Variant of External Vacuum Aspiration in the Treatment of Purulent Diseases of Soft Tissues," in *Current Problems in Modern Clinical Surgery*, Volkov, V.Y. et al. eds.,

(56) References Cited

OTHER PUBLICATIONS

Cheboksary: Chuvashia State University, 14 pages. (includes English translation and translation certifications).
Chariker, M.E. et al. (Jun. 1989). "Effective Management of Incisional and Cutaneous Fistulae with Closed Suction Wound Drainage," *Contemporary Surgery* 34:59-63.
Davydov, Y.A. et al. (Sep. 1986). "Vacuum Therapy in the Treatment of Purulent Lactation Mastitis," *The Kremlin Papers: Perspectives in Wound Care* pp. 5-7.
Davydov, Y.A. et al. (Oct. 1988). "The Bacteriological and Cytological Assessment of Vacuum Therapy of Purulent Wounds," *The Kremlin Papers: Perspectives in Wound Care* pp. 11-14.
Davydov, Y.A. et al. (Feb. 1991). "Concepts for Clinical Biological Management of the Wound Process in the Treatment of Purulent Wounds Using Vacuum Therapy," *The Kremlin Papers: Perspectives in Wound Care* pp. 15-17.
Final Office Action dated Apr. 21, 2010, for U.S. Appl. No. 12/047,739, filed Mar. 13, 2008, 16 pages.
Final Office Action dated Apr. 22, 2010, for U.S. Appl. No. 12/234,530, filed Sep. 19, 2008, 16 pages.
Herrmann, L.G. et al. (1934). "The Conservative Treatment of Arteriosclerotic Peripheral Vascular Diseases: Passive Vascular Exercises (Pavaex Therapy)," *Ann. Surgery* pp. 750-760.
International Preliminary Report on Patentability dated Sep. 24, 2009, for PCT Application No. PCT/US2008/003412, filed Mar. 13, 2008, seven pages.
International Preliminary Report on Patentability dated Jun. 9, 2011, for PCT Application No. PCT/US2009/065959, filed Nov. 25, 2009, nine pages.
International Search Report dated Jul. 28, 2008, for PCT Application No. PCT/US08/03412, filed Mar. 13, 2008, three pages.
International Search Report dated May 29, 2009, for PCT Application No. PCT/US2009/034158, filed Feb. 13, 2009, two pages.
International Search Report dated Jan. 21, 2010, for PCT Application No. PCT/US09/65959, filed on Nov. 25, 2009, five pages.
International Search Report dated May 4, 2010, for PCT Application No. PCT/US2010/026269, filed on Mar. 4, 2010, four pages.
Kostiuchenok, B.M. et al. (Sep. 1986). "The Vacuum Effect in the Surgical Treatment of Purulent Wounds," *The Kremlin Papers: Perspectives in Wound Care* pp. 3-4.
Meyer, D.C. et al. (Jun. 2005). "Weight-Loaded Syringes as a Simple and Cheap Alternative to Pumps for Vacuum-Enhanced Wound Healing," *Plastic and Reconstructive Surgery* 115(7):2174-2176, located at <http://gateway.tx.ovid.com.laneproxy.stanford.edu/gw2/ovidweb.cgi>, last visited on Oct. 15, 2007.
Non-Final Office Action dated Oct. 29, 2009, for U.S. Appl. No. 12/234,530, filed Sep. 19, 2008, 14 pages.
Non-Final Office Action dated Nov. 27, 2009, for U.S. Appl. No. 12/047,739, filed Mar. 13, 2008, 18 pages.
Non-Final Office Action dated Oct. 12, 2011, for U.S. Appl. No. 12/626,426, filed Nov. 25, 2009, 14 pages.
Non-Final Office Action dated Oct. 31, 2011, for U.S. Appl. No. 13/030,042, filed Feb. 17, 2011, 17 pages.
Non-Final Office Action dated Nov. 2, 2011, for U.S. Appl. No. 12/646,856, filed Dec. 23, 2009, 15 pages.
Non-Final Office Action dated Nov. 18, 2011, for U.S. Appl. No. 13/245,735, filed Sep. 26, 2011, 13 pages.
Non-Final Office Action dated Dec. 23, 2011, for U.S. Appl. No. 13/245,746, filed Sep. 26, 2011, 10 pages.
Non-Final Office Action dated Feb. 13, 2012, for U.S. Appl. No. 12/047,739, filed Mar. 13, 2008, 11 pages.
Notice of Allowance dated Jun. 24, 2011, for U.S. Appl. No. 12/234,530, filed Sep. 19, 2008, 11 pages.
Notice of Allowance dated Dec. 22, 2011, for U.S. Appl. No. 12/760,406, filed Apr. 14, 2010, eight pages.
Pre-Interview First Office Action dated Dec. 15, 2011, for U.S. Appl. No. 12/372,661, filed Feb. 17, 2009, three pages.
Svedman, P. (Sep. 3, 1983). "Irrigation Treatment of Leg Ulcers," *The Lancet* pp. 532-534.

Svedman, P. et al. (Aug. 1986). "A Dressing System Providing Fluid Supply and Suction Drainage Used for Continuous or Intermittent Irrigation," *Annals of Plastic Surgery* 17(2):125-133.
Ubbink, D.T. et al. (2009). "Topical Negative Pressure for Treating Chronic Wounds," *The Cochrane Collaboration* 3:1-32.
Urschel, J.D. et al. (1988). "The Effect of Mechanical Stress on Soft and Hard Tissue Repair; a Review," *British Journal of Plastic Surgery* 41:182-186.
Usupov, Y.N. et al. (Apr. 1987). "Active Wound Drainage," *The Kremlin Papers: Perspectives in Wound Care* pp. 8-10.
Written Opinion dated May 4, 2010, for PCT Application No. PCT/US2010/026269, filed on Mar. 4, 2010, seven pages.
Written Opinion of the International Searching Authority dated Jan. 21, 2010, for PCT Application No. PCT/US09/65959, filed on Nov. 25, 2009, seven pages.
Non Final Office Action received for U.S. Appl. No. 13/030,042, dated May 8, 2013, 19 pages.
Notice of Allowance received for U.S. Appl. No. 13/245,746, dated May 29, 2013, 10 pages.
Non Final Office Action received for U.S. Appl. No. 12/047,739, dated Jun. 21, 2013, 12 pages.
Advisory Action received for U.S. Appl. No. 12/717,838, dated Jul. 5, 2013, 2 pages.
"3M Tegaderm Hydrocolloid Dressing", Sacral-6-¾"×6-⅜", 1 page.
"Adhesive Sacral Dressing", Smith & Nephew, 3 pages.
EuroMed, "Hydrocolloid Health Technologies", Product Catalog, 11 pages.
"Mask—Medical Definition and More from Merriam-Webster", available at <http://www.merriam-webster.com/medical/mask>, accessed on Aug. 25, 2012, 2 pages.
"Atmosphere—Definition from the Merriam-Webster Online Dictionary", available at <http://www.merriam-webster.com/dictionary/atmosphere>, accessed on Nov. 20, 2009, 2 pages.
PolyMem QuadraFoam, Case Study, "Huge Sacral Pressure Ulcer Closed in Four Months Using PolyMem Silver and PolyMem Wic Silver Dressings", Presented at 17th Conference of the European Wound Management Association, Poster #135, May 2-4, 2007, Glasgow, Scotland, 2 pages.
"PolyMem Quadrafoam", located at <http://www.verebrun.com>, 4 pages.
Office Action received for Japanese Patent Application No. 2010-546944, dated Jun. 19, 2012, 4 pages.
International Search Report and Written Opinion received for PCT Patent Application No. PCT/US2010/020368, dated Feb. 26, 2010, 7 pages.
International Preliminary Report on Patentability received for PCT Patent Application No. PCT/US2009/034158, dated Aug. 17, 2010, 8 pages.
International Preliminary Report on Patentability received for PCT Patent Application No. PCT/US2010/020368, dated Jul. 12, 2011, 6 pages.
International Preliminary Report on Patentability received for PCT Patent Application No. PCT/US2010/026269, dated Sep. 15, 2011, 9 pages.
Non Final Office Action received for U.S. Appl. No. 12/234,530, dated Nov. 16, 2010, 14 pages.
Notice of Allowance received for U.S. Appl. No. 13/245,735, dated Mar. 7, 2012, 7 pages.
Notice of Allowance received for U.S. Appl. No. 12/372,661, dated Apr. 9, 2012, 5 pages.
Non Final Office Action received for U.S. Appl. No. 12/717,838, dated Jun. 28, 2012, 14 pages.
Notice of Allowance received for U.S. Appl. No. 12/760,409, dated Jul. 17, 2012, 16 pages.
Final Office Action received for U.S. Appl. No. 12/646,856 dated Jul. 26, 2012, 18 pages.
Final Office Action received for U.S. Appl. No. 12/626,426, dated Aug. 31, 2012, 22 pages.
Final Office Action received for U.S. Appl. No. 13/030,042, dated Aug. 31, 2012, 21 pages.
Non Final Office Action received for U.S. Appl. No. 12/683,987, dated Nov. 5, 2012, 21 pages.

(56) References Cited

OTHER PUBLICATIONS

Final Office Action received for U.S. Appl. No. 12/047,739, dated Nov. 7, 2012, 12 pages.
Notice of Allowance received for U.S. Appl. No. 12/683,987, dated Dec. 10, 2012, 7 pages.
Fletcher, Jacqui, "World Wide Wounds, Dressings: Cutting and Application Guide", May 2007, available at: <http://www.worldwidewounds.com/2007/may/Fletcher/Fletcher-Dressings-Cutting-Guide.html>, 15 pages.
Girolami, Susan, "Bio-Dome™ Technology: The Newest Approach to Negative Pressure Wound Therapy", 1 page.
Gokoo et al., "Evaluation of a Sacral Shaped Transparent Dressing Over Contoured and High Stress Areas", 3M Health Care, 1997, 4 pages.
Gupta et al., "Differentiating Negative Pressure Wound Therapy Devices: An Illustrative Case Series", Wounds, vol. 19, No. 1, Jan. 2007, pp. 1-9.
Wicks, Gill, "A Guide to the Treatment of Pressure Ulcers from Grade 1-Grade 4", Wound Essentials, vol. 2, 2007, 106,108,110,112-113 pages.
Written Opinion received for PCT Patent Application No. PCT/US2009/034158, dated May 29, 2009, 7 pages.
Written Opinion received for PCT Patent Application No. PCT/US2008/003412, dated Jul. 28, 2008, 5 pages.
Office Action received for Australian Patent Application No. 2009214439, dated May 9, 2013, 3 pages.
Office Action received for Chinese Patent Application No. 200980112984.X, dated Aug. 16, 2013, 11 pages.
Office Action received for Chinese Patent Application No. 200980112984.X, dated Dec. 4, 2012, 13 pages.
Office Action received for Japanese Patent Application No. 2012-229673, dated Sep. 17, 2013, 5 pages.
Final Office Action received for U.S. Appl. No. 12/047,739, dated Feb. 13, 2014, 16 pages.
"McGraw-Hill Dictionary of Scientific and Technical Terms", 6th edition, 2003, 2 pages.
Computer Language Company Inc., "Computer Desktop Encyclopedia (CDE)", 1981, 2 pages.
Extended European Search Report (includes Supplementary European Search Report and Search Opinion) received for European Patent Application No. 08726845.4, dated Jun. 20, 2014, 7 pages.
Extended European Search Report (includes Supplementary European Search Report and Search Opinion) received for European Patent Application No. 14187150.9, dated Dec. 10, 2014, 6 pages.
Intention to Grant received for European Patent Application No. 09709714.1, dated Apr. 29, 2014, 8 pages.
Intention to grant received for European Patent Application No. 09832371.0, dated Jun. 2, 2014, 5 pages.
Office Action received for European Patent Application No. 09832371.0, dated Oct. 30, 2013, 5 pages.
Non Final Office Action received for U.S. Appl. No. 12/047,739, dated May 15, 2015, 15 pages.
Final Office Action received for U.S. Appl. No. 12/626,426, dated Jan. 3, 2014, 11 pages.
Non-Final Office Action received for U.S. Appl. No. 12/626,426, dated Dec. 23, 2014, 14 pages.
Advisory Action received for U.S. Appl. No. 12/646,856, dated Jan. 29, 2014, 3 pages.
Final Office Action received for U.S. Appl. No. 12/646,856, dated Nov. 4, 2013, 19 pages.
Notice of Allowance received for U.S. Appl. No. 12/717,838, dated Jan. 8, 2014, 10 pages.
Non-Final Office Action received for U.S. Appl. No. 13/020,685, dated Feb. 14, 2014, 9 pages.
Notice of Allowance received for U.S. Appl. No. 13/020,685, dated Oct. 15, 2014, 9 pages.
Final Office Action received for U.S. Appl. No. 13/030,042, dated Mar. 14, 2014, 26 pages.
Non-Final Office Action received for U.S. Appl. No. 13/030,042, dated Apr. 10, 2015, 27 pages.

Non Final Office Action received for U.S. Appl. No. 13/077,857, dated Apr. 24, 2015, 9 pages.
Non-Final Office Action received for U.S. Appl. No. 13/077,857, dated Jul. 17, 2014, 12 pages.
Notice of Allowance received for U.S. Appl. No. 13/615,173, dated Sep. 24, 2014, 7 pages.
Final Office Action received for U.S. Appl. No. 13/752,206, dated Oct. 31, 2014, 12 pages.
Non Final Office Action received for U.S. Appl. No. 13/752,206, dated Apr. 23, 2015, 6 pages.
Non-Final Office Action received for U.S. Appl. No. 13/752,206, dated Apr. 29, 2014, 14 pages.
Notice of Allowance received for U.S. Appl. No. 13/752,206, dated Oct. 7, 2015, 7 pages.
Notice of Acceptance received for Australian Patent Application No. 2009214439, dated Sep. 10, 2014, 2 pages.
Office Action received for Australian Patent Application No. 2009214439, dated Jul. 1, 2014, 4 pages.
Office Action received for Australian Patent Application No. 2009324913, dated Feb. 24, 2015, 4 pages.
Notice of Allowance received for Canadian Patent Application No. 2,715,645, dated Mar. 12, 2015, 1 page.
Office Action received for Chinese Patent Application No. 200980112984.X, dated Mar. 19, 2014, 4 pages (2 pages of English Translation and 2 pages of official copy).
Office Action received for Japanese Patent Application No. 2010-546944, dated Apr. 1, 2013, 5 pages (3 pages of English Translation and 2 pages of official copy).
Office Action received for Japanese Patent Application No. 2011-537745, dated Apr. 15, 2014, 4 pages (2 pages of English Translation and 2 pages of Official Copy).
Office Action received for Japanese Patent Application No. 2011-537745, dated Dec. 6, 2013, 7 pages (4 pages of English Translation and 3 pages of official copy).
Office Action received for Japanese Patent Application No. 2012-229673, dated May 30, 2014, 4 pages (2 pages of English Translation and 2 pages of Official Copy).
Notice of Allowance received for Japanese Patent Application No. 2010-546944, dated Mar. 3, 2014, 3 pages of Official Copy only. (See Communication under 37 CFR § 1.98(a) (3).
Notice of Allowance received for Japanese Patent Application No. 2011-537745, dated Dec. 10, 2014, 3 pages of Official Copy only. (See Communication under 37 CFR § 1.98(a) (3).
Notice of Allowance received for Japanese Patent Application No. 2012-229673, dated Dec. 16, 2014, 3 pages of Official Copy only. (See Communication under 37 CFR § 1.98(a) (3).
Office Action received for Japanese Patent Application No. 2012-229674, dated Nov. 20, 2013, 2 pages of Official Copy only. (See Communication under 37 CFR § 1.98(a) (3).
Office Action received for Japanese Patent Application No. 2012-229674, dated Nov. 27, 2014, 2 pages of Official Copy only. (See Communication under 37 CFR § 1.98(a) (3).
Partial ISR for corresponding PCT/US2017/018129, dated May 15, 2017.
Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.

(56) References Cited

OTHER PUBLICATIONS

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov I").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

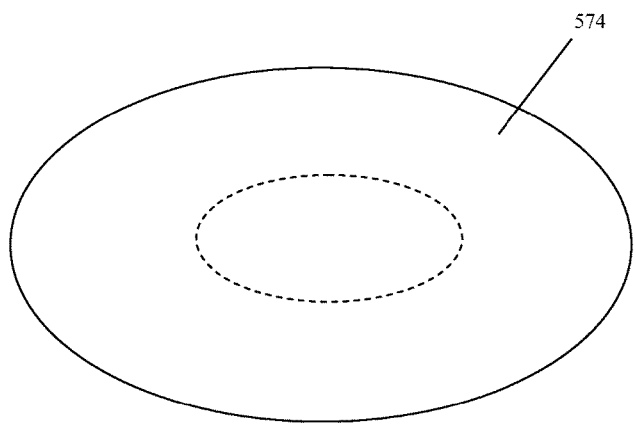
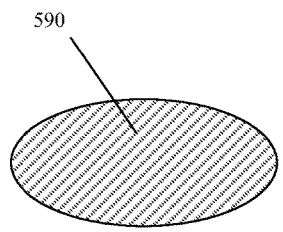
FIG. 5A  FIG. 5B
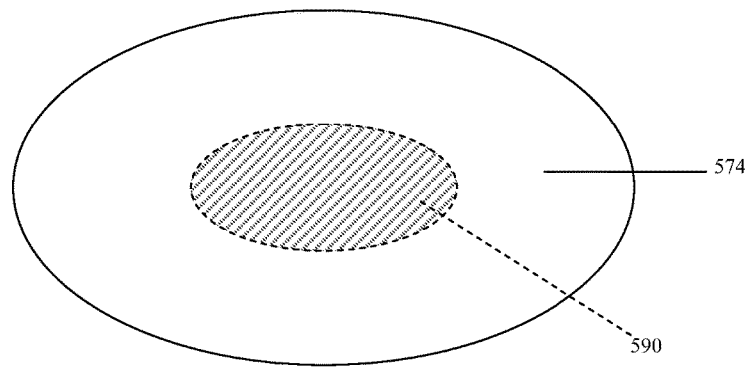
FIG. 5C

REDUCED PRESSURE THERAPY DEVICES

CROSS-REFERENCE TO RELATED APPLICATIONS

This application is a continuation of U.S. patent application Ser. No. 12/234,530, filed on Sep. 19, 2008, which is a continuation of U.S. patent application Ser. No. 12/047,739, filed on Mar. 13, 2008, which claims priority under 35 U.S.C. § 119(e) to a) U.S. Provisional Application Ser. No. 60/973,086, filed on Sep. 17, 2007, and b) U.S. Provisional Application Ser. No. 60/906,721, filed Mar. 14, 2007, all of which are hereby incorporated by reference in their entirety.

BACKGROUND

The present invention relates generally to wound therapy devices, including reduced pressure therapy devices and the suction applied by reduced pressure therapy devices.

Medical practice commonly uses suction devices to improve drainage of fluids from the body of a patient. For example, suction devices are routinely used to speed wound drainage following surgery. One type of wound suction device includes a portable, relatively small suction chamber which is coupled to a source of body fluids. Applying reduced pressure to a wound may have several beneficial effects. One effect that it has is that the reduced pressure draws out exudate and necrotic tissue, which might contain dirt and bacteria, from the wound to further promote healing. Other benefits of applying reduced pressure to a wound include increasing perfusion to the wound and reduction of edema. Still other benefits of reduced pressure include retraction of the wound edges into the dressing, and removal of matrix metalloproteinase enzymes which inhibit granulation of tissue, and are related to tissue healing and remodeling, as well as to cancer metastasis. One other advantage of reduced pressure therapy is the fact that mechanical stimulation causes the natural release of growth factors by the cells in the wound body. All these benefits help to further promote wound healing.

Due to the benefits of reduced pressure therapy, it would be beneficial to develop reduced pressure therapy devices.

BRIEF SUMMARY

Generally described herein are tissue therapy devices. In one embodiment, the device comprises a sealant layer and a suction apparatus in fluid communication through the sealant layer. The sealant layer may be adapted and configured to create a seal around an area of tissue requiring therapy. The suction apparatus may be adapted and configured to reduce pressure underneath the sealant layer. In addition, the suction apparatus may be adapted and configured to self-create the reduced pressure under the sealant layer. Moreover, the suction apparatus may be non-electrically powered. In some embodiments, the sealant layer and the suction apparatus form a closed reduced pressure system. In such embodiments, the closed system is resistant or not susceptible to the back streaming of gas. In some embodiments, the device is adapted and configured to create a generally airtight seal. In some embodiments, the device is adapted and configured to reduce pressure underneath the sealant layer by expanding the volume of air located in a joint volume of space shared between the sealed enclosure and the suction apparatus. In one embodiment of the device provided herein, the device delivers equivalent pressure levels and mechanical stimuli to the area to be treated. In a further embodiment, the device is configured to expand the volume of the enclosure by decreasing the density of air molecules under the sealant layer. In some embodiments, the device may be adapted and configured to maintain the reduced pressure that it creates.

In some embodiments, the level of reduced pressure may be applied and maintained for short periods of time or for extended periods of time. The reduced pressure may be applied and maintained for as short as approximately thirty (30) minutes or for as long as over 4 weeks or more. In some embodiments, the reduced pressure is applied for longer than 30 minutes. In some embodiments, the reduced pressure is applied for longer than 24 hours. In some embodiments, the reduced pressure is applied for longer than several days. In some embodiments, the reduced pressure is applied for longer than one week. In some embodiments, the reduced pressure is applied for longer than 4 weeks. In some embodiments, the device may incorporate an additional external suction apparatus if so desired.

In some embodiments, the reduced pressure is maintained by a ratcheting mechanism integrated with the suction apparatus. In some embodiments of the device, the suction apparatus also serves as a collection chamber. In some embodiments, the device further comprises an external collection chamber. In some embodiments, the tissue therapy device described herein further comprises a second suction apparatus.

In some embodiments, the device comprises a suction apparatus and a sealant layer in which the suction apparatus and sealant layer are separate structures. In some embodiments, the suction apparatus and the sealant layer are integrated into a single structure. In some embodiments of the device described herein, the suction apparatus may be disconnected from the sealant layer, emptied, and then reconnected to the sealant layer. In some embodiments of the device provided herein, the suction apparatus is disconnected and discarded. In such an embodiment, the suction apparatus may be replaced with a new second suction apparatus. In a further embodiment of the device, where the suction apparatus is replaced with a second suction apparatus, the second suction apparatus may be replaced with a suction apparatus that is of the same type as the first suction apparatus. In some embodiments, the second suction apparatus is different than the first suction apparatus. In some embodiments where the suction apparatus may be detached, the suction apparatus may be configured to be detached and reattached without disturbing the sealant layer or the airtight seal between the sealant layer and the skin of the patient.

In some of the embodiments, the tissue therapy device further comprises a one-way flow valve. In such an embodiment, the one-way flow valve may be adapted and configured to prevent exudate from returning to the section of tissue for which therapy is required and to which the reduced pressure is applied.

In some embodiments of the device, the device is configured to be portable. In a further embodiment of the device, the device is configured to be secured to the patient. Yet in other embodiments the device is configured to be wearable.

In some further embodiments, a tissue therapy device is provided, comprising a sealant layer, a suction apparatus, and a contact layer. In some embodiments of the device, the contact layer comprises a stacked mesh matrix. In some embodiments of the device, the contact layer and the sealant layer are separate structures. In some embodiments of the device, the contact layer and the sealant layer are integrated into a single structure. In another embodiment of the device, at least any two of the suction apparatus, the contact layer, or the sealant layer are integrated together while the third remains a separate structure. In some embodiments, the contact layer and the sealant layer are integrated together and the suction apparatus is a separate structure. In some embodiments, the contact layer and the suction apparatus are integrated together and the sealant layer is a separate structure. In some embodiments, the sealant layer and the suction apparatus are integrated together and the contact layer is a separate structure.

In some embodiments, the device further comprises a protective layer. The protective layer is placed around the area of tissue to be treated. In some embodiments the protective layer can be any suitable biocompatible polymer. In some embodiments of the device, the sealant layer may be any suitable biocompatible polymer.

In another embodiment, a mesh matrix is provided, comprising at least one mesh matrix sheet. In some embodiments, at least two mesh matrix sheets may be provided, wherein the mesh matrix sheets are adapted and configured to provide fluid communication between a suction apparatus and an area of damaged tissue. In some embodiments, the mesh matrix comprises two or more mesh matrix sheets. In some embodiments, multiple mesh matrix sheets may be arranged in stacked or layered configuration. The mesh matrix sheets may be separated to a desired thickness. In some embodiments, the mesh matrix sheet may be cut such that it conforms to an area or shape of tissue damage. In a further embodiment, the mesh matrix sheet comprises filaments. In some embodiments, the filaments are made of a polymer. In some embodiments, the filaments are aligned perpendicular or another angle to each other throughout the stacked mesh matrix. In other embodiments, the filaments are randomly oriented with respect to each other. In some embodiments, the filaments of the stacked mesh matrix are hollow. In some embodiments, the stacked mesh matrix further comprises a delivery mesh as one of the layers of the stacked mesh matrix. In some embodiments, the filaments of the delivery mesh are hollow.

In some embodiments, the contact layer of the tissue therapy device comprises an adjustable pouch containing one or more non-filamentous structures. The non-filamentous structures and the pouch may be adapted and configured to provide fluid communication between the suction apparatus and the area of tissue requiring treatment. In some embodiments the non filaments structures are made from a biocompatible polymer material. In some embodiments the pouch contains at least two structures. In some embodiments the pouch volume can be adjusted by adding or subtracting non-filamentous structures from the pouch without disturbing the integrity of the pouch.

In another embodiment, a method for applying reduced pressure therapy to an area of tissue is provided, comprising creating a sealed enclosure around an area of tissue to be treated by affixing a sealant layer to a surface of a patient. Reduced pressure is then self-created underneath the sealant layer by expanding the volume of air located in the enclosed space, the enclosed space including the joint volume of air located underneath the sealant layer and the volume of air located in internal volume of the suction apparatus. Expanding this joint volume may decrease the density of air molecules located throughout the volume of space and reduce the pressure under the sealant layer. In some embodiments, the method uses a closed reduced pressure therapy system comprising a sealant layer and the suction apparatus. In some embodiments, the sealed enclosure is air-tight. In some embodiments, the method further comprises providing a contact layer on the wound surface before the sealant layer is affixed to the surface of the patient. In some embodiments, the method further comprises applying a protective layer around the area of the tissue to be treated before creating the sealed enclosure. In some embodiments, the method further comprises applying a hydrocolloid to the area of tissue to be treated. In some embodiments, the dressing may be pre-configured with a hydrocolloid layer.

In one embodiment, a method of treating a wound using a reduced pressure therapy device is provided, comprising creating a sealed enclosure between a sealant layer of a wound dressing and the surface of a patient and applying self-created reduced pressure to a wound by forcefully expanding a volume of air molecules enclosed in the sealed enclosure. In some embodiments, the method uses a closed reduced pressure therapy system. In some embodiments, the wound to be treated is selected from an acute wound, a partial- or full-thickness burn, a surgically created wound or surgical dehiscence, neuropathic (e.g. diabetic) wounds, venous or arterial insufficiency ulcers, traumatic wounds, and pressure ulcers, and any other wound or damaged tissue for which the application of reduced pressure therapy is suitable.

In still another embodiment, a method of treating an area of damaged tissue using reduced pressure tissue therapy is provided, comprising positioning a reduced pressure tissue therapy device over an area of tissue to be treated, where the reduced pressure tissue therapy device comprises a sealant layer and a suction apparatus, and reducing the level of pressure in a volume of air located under the sealant layer by engaging the suction apparatus, where the suction apparatus self-creates the reduction in pressure by forcefully expanding the volume of air. In some embodiments, the sealant layer and the suction apparatus form a closed reduced tissue therapy system. In some embodiments of the method described herein, the method further comprises decreasing the density of air molecules under the sealant layer to create reduced pressure.

In one embodiment, a tissue therapy device is provided, comprising a sealant layer, said sealant layer adapted and configured to create a sealed enclosure around an area of tissue requiring therapy, and a suction apparatus, said suction apparatus in fluid communication through the sealant layer with said enclosure and adapted and configured to self-create a reduced pressure level within said enclosure, wherein said sealant layer and said suction apparatus are adapted and configured to create a closed reduced pressure system, wherein the suction apparatus is configured to be portable. The sealant layer may be adapted and configured to create an airtight seal. The suction apparatus may be adapted and configured to expand a volume of air located in a joint volume of space shared between said sealed enclosure and said suction apparatus, and/or may be adapted and configured to decrease a density of air molecules under the sealant layer when said suction apparatus is engaged. In some embodiments, the suction apparatus may self-create a level of reduced pressure underneath said sealant layer, wherein said level of reduced pressure is between about 0 and about 760 mm Hg. The sealant layer shape may follow a perimeter of the area of tissue undergoing therapy. The device may be further adapted and configured to maintain a level of reduced pressure of between about 0 and about 760 mm Hg. The device may also be further adapted and configured to maintain a level of reduced pressure for an extended period of time. The suction apparatus may further comprise a retaining mechanism, and in some embodiments, the retaining mechanism is a ratcheting mechanism. The suction apparatus may further comprise a collection chamber, which may be an internal or an external collection chamber. The device may also further comprise a second suction apparatus. The suction apparatus and the sealant layer may be two separate structures, or may be integrated into a single structure. The suction apparatus may be adapted and configured to be disconnected from the sealant layer, emptied, and reconnected to the sealant layer, and in some embodiments, may be performed without disturbing the sealant layer. In some embodiments, the device may further comprise a second suction apparatus, wherein the second suction apparatus is adapted and configured to be connected to the sealant layer. The second suction apparatus may have a similar or a different configuration as the first suction apparatus. The suction apparatus may also further comprises a safety valve and/or a one-way flow valve, wherein said one-way flow valve is adapted and configured to prevent fluid from returning to the section of tissue requiring therapy. The suction apparatus is adapted and configured to be secured to a patient. The device may further comprise a securing member configured to attach the suction apparatus to a patient. The device may also further comprise a contact layer, which is may be a stacked mesh matrix. The contact layer and the sealant layer may be at least two separate structures or may be integrated into a single structure. In some embodiments, at least any two of the suction apparatus, the contact layer, or the sealant layer are integrated together while the third is a separate structure. For example, the contact layer and the sealant layer may be integrated together and the suction apparatus is a separate structure, or the contact layer and the suction apparatus are integrated together and the sealant layer is a separate structure. In another example, the sealant layer and the suction apparatus are integrated together and the contact layer is a separate structure. The device may also further comprise a protective layer placed around the area of tissue to be treated. In some embodiments, the sealant layer and/or the protective layer may be any biocompatible polymer.

In another embodiment, a tissue therapy device is provided, comprising a sealant layer, said sealant layer adapted and configured to create a sealed enclosure around an area of tissue, and a non electrically powered suction apparatus, said suction apparatus in fluid communication through the sealant layer with said enclosure and adapted and configured to self-create a reduced pressure level underneath the sealant layer, wherein said sealant layer and said suction apparatus are adapted and configured to create a closed reduced pressure system, wherein the suction apparatus is configured to be wearable.

In some embodiments, a stacked mesh matrix is provided, comprising at least two mesh matrix sheets, wherein said mesh matrix sheets are adapted and configured to provide fluid communication between a suction apparatus and an area of damaged tissue. The stacked mesh matrix may comprise multiple mesh matrix sheets. In some embodiments, mesh matrix sheets are further adapted and configured to be separated from each other. In some embodiments, at least one mesh matrix sheet is further adapted and configured to be cut to conform to the area of tissue damage. The mesh matrix sheets may comprise polymer filaments. The polymer filaments may be generally aligned perpendicular to each other, or may be non-uniformly oriented. The polymer filaments may have an average thickness of about 10 mm or less, or sometimes between about 0.001 mm and to about 10 mm in thickness. The polymer filaments may have of a uniform thickness, non-uniform thickness, or a random thickness throughout the stacked mesh matrix. In one embodiment, the polymer filaments of said mesh matrix sheet are about 1 mm to about 15 mm apart in spacing. The polymer filaments may be spaced a non-uniform or a uniform distance apart throughout the stacked mesh matrix. The polymer filaments may be hollow. The stacked mesh matrix may further comprise a delivery mesh matrix as one layer of the mesh matrix. The delivery mesh matrix may also comprise hollow polymer filaments.

In some embodiments, a contact layer is provided, comprising at least one non-planar structure adapted to provide fluid communication between the suction apparatus and the area of tissue requiring treatment. The non-planar structures are packed into adjustable porous pouch adapted to facilitate placement and replacement of said structure into the tissue cavity.

In another embodiment, a method of applying reduced pressure therapy to an area of tissue is provided, comprising creating a sealed enclosure around an area of tissue to be treated by affixing a sealant layer around said area of tissue to be treated, self-creating a reduced pressure underneath the sealant layer by expanding a volume of said sealed enclosure using a suction apparatus, wherein said suction apparatus is in fluid communication through the sealant layer, wherein said sealant layer and said suction apparatus are adapted and configured to create a closed reduced pressure system, and securing said suction apparatus to a patient. The sealed enclosure may be substantially air-tight. The method may further comprise positioning a contact layer on the wound surface before said sealant layer is affixed. The method may further comprise applying a protective layer around the area of tissue to be treated before creating the sealed enclosure. The contact layer may be a stacked mesh matrix. The method may further comprise applying a hydrocolloid over the area of tissue to be treated.

In some embodiments, a method of treating a wound using a reduced pressure therapy device is provided, comprising creating a sealed enclosure around a wound by covering said wound with a sealant layer of a wound dressing, applying a reduced pressure to the wound using a suction apparatus, wherein said suction apparatus self-creates said reduced pressure by expanding a volume of air molecules located underneath said sealed enclosure, wherein said sealant layer and said suction apparatus are adapted and configured to create a closed reduced pressure system, and securing said suction apparatus to a patient. The wound may be a wound selected from the a group consisting of an acute wound, a partial- or full-thickness burn, a surgically created wound or surgical dehiscence, neuropathic (diabetic) wounds, venous or arterial insufficiency ulcers, traumatic wounds, and pressure ulcers, or any other wound for which reduced pressure therapy may be a suitable method of treatment.

In one embodiments, a method of treating a wound using a reduced pressure tissue therapy device is provided, comprising positioning a reduced pressure tissue therapy device over an area of tissue to be treated, said reduced pressure tissue therapy device comprising a sealant layer and a suction apparatus, reducing a level of pressure in a volume of air located under the sealant layer by engaging the suction apparatus, wherein said engaging of said suction apparatus self-creates a reduction in pressure by expanding said volume of air, wherein said sealant layer and said suction apparatus are adapted and configured to create a closed reduced pressure system, and securing said suction apparatus to a patient. The reduced pressure tissue therapy device may decrease a density of air molecules under the sealant layer to create reduced pressure. In some embodiments, the method further comprises applying a contact layer to the area of tissue. Sometimes, applying the contact layer occurs between affixing the sealant layer and before creating a sealed enclosure.

BRIEF DESCRIPTION OF THE DRAWINGS

A better understanding of various features and advantages of the present invention will be obtained by reference to the following detailed description that sets forth illustrative embodiments, in which the principles of the invention are utilized, and the accompanying drawings of which:

FIG. 1A is an illustration of one embodiment of a wound dressing and a suction apparatus attached to the wound dressing. FIG. 1B illustrates one embodiment of the sealant layer of a wound dressing.

FIG. 3 illustrates the wound dressing placed on the patient to which the suction apparatus is attached. FIG. 3 further illustrates the portability of the tissue therapy device as shown by the device being secured to the patient.

FIGS. 5A to 5C show one embodiment of an illustration of a protective layer and its use. FIG. 5A shows one embodiment of a protective layer that may be cut to the size of the wound depicted in FIG. 5B. FIG. 5C shows the protective layer of FIG. 5A as placed around the wound of FIG. 5B.

FIG. 9A is a side illustration of a stacked mesh matrix with an integrated delivery mesh placed under a sealant layer. FIG. 9B is a side illustration of a delivery mesh in fluid communication with a solution reservoir as placed under a sealant layer wherein positive pressure is applied to the wound simultaneously with a solution to enhance infusion of the solution into the wound. FIG. 9C shows the delivery mesh after infusion has ended and where the suction apparatus applies negative pressure under traditional reduced pressure therapy.

DETAILED DESCRIPTION

Figure 1A:
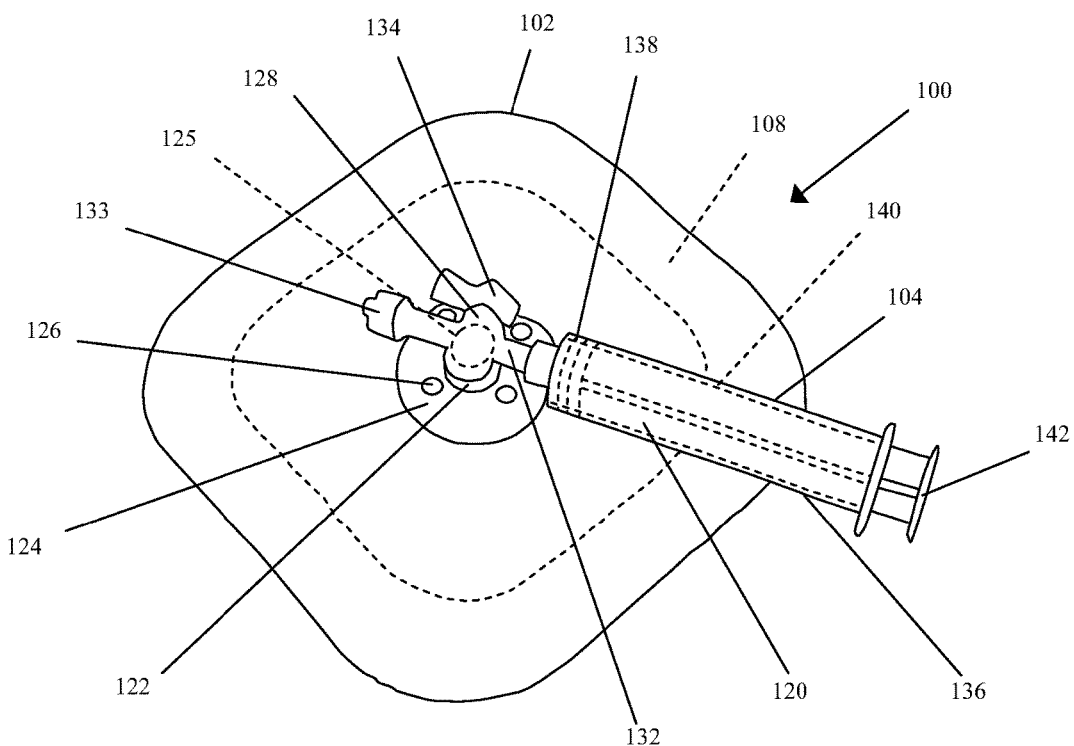
FIGS. 1A and 1B are perspective views of one embodiment of a reduced pressure tissue therapy device.

Current negative pressure wound therapy (NPWT) systems use large, electrically driven mechanical pumps to deliver negative pressure to the treatment site. These pumps, however, limit a patient's mobility, requiring that the patient be connected to the system as well as a bulky power source throughout the course of treatment. NPWT is also very expensive, with the pump accounting for the majority of the costs.

Described generally herein are devices adapted and configured to provide reduced pressure to an area of tissue. Application of reduced pressure to an area of tissue may be used to create a therapeutic effect. In one embodiment what is described herein is a tissue therapy device. The device may be used to treat areas of tissue to which damage has occurred. In other embodiments the device may be used on non-damaged tissue.

In one embodiment, the tissue therapy device comprises a sealant layer and a suction apparatus. The sealant layer creates a seal around an area of tissue requiring therapy. The suction apparatus reduces pressure underneath the sealant layer. The reduction in pressure is self-created by the suction apparatus. In some embodiments the suction apparatus is non-electrically powered. In some embodiments, the sealant layer and the suction apparatus form a closed reduced pressure system. In such an embodiment, the closed system is not susceptible or resistant to the back streaming of gas. When the sealant layer is placed in contact with the patient, an airtight seal may be formed between the area surrounding the area of tissue to be treated and the sealant layer thereby creating a sealed enclosure. The suction apparatus then self-creates reduced pressure by expanding the volume of air located in a joint volume of space shared between the sealed enclosure and the suction apparatus by decreasing the density of the air molecules located in the volume of space created by the sealed enclosure. The suction apparatus may also serve as a collection chamber for collecting exudate drawn up out of the wound, for example.

In some embodiments, the suction apparatus is configured to self-create reduced pressure. When first positioned on the patient, the pressure underneath the sealed enclosure is typically at a pressure equal to the ambient atmospheric pressure. When the device is engaged, the level of pressure may be reduced. The level of pressure may be reduced to a therapeutic level. The device may self-create a reduced pressure underneath the sealant layer where the reduced pressure is anywhere between about 0 and about 760 millimeters of Mercury (mm Hg). In some embodiments, the device is adapted and configured to self-create a level of reduced pressure between approximately 0 and approximately 760 mm Hg. In some embodiments, the self-created level of reduced pressure in the enclosure formed by the sealant layer is more than approximately 10 mm Hg. In some embodiments, the self-created level of reduced pressure in the enclosure formed by the sealant layer is more than approximately 20 mm Hg. In some embodiments, the self-created level of reduced pressure in the enclosure formed by the sealant layer is more than approximately 50 mm Hg. In some embodiments, the self-created level of reduced pressure in the enclosure formed by the sealant layer is more than approximately 80 mm Hg. In some embodiments, the self-created level of reduced pressure in the enclosure formed by the sealant layer is more than approximately 100 mm Hg. In some embodiments, the self-created level of reduced pressure in the enclosure formed by the sealant layer is more than approximately 150 mm Hg. In some embodiments, the self-created level of reduced pressure in the enclosure formed by the sealant layer is more than approximately 200 mm Hg. In some embodiments, the self-created level of reduced pressure in the enclosure formed by the sealant layer is more than approximately 500 mm Hg. In some embodiments, the self-created level of reduced pressure in the enclosure formed by the sealant layer is more than approximately 700 mm Hg. In some embodiments, the self-created level of reduced pressure in the enclosure formed by the sealant layer is less than approximately 750 mm Hg. In some embodiments, the self-created level of reduced pressure in the enclosure formed by the sealant layer is less than approximately 700 mm Hg. In some embodiments, the self-created level of reduced pressure in the enclosure formed by the sealant layer is less than approximately 600 mm Hg. In some embodiments, the self-created level of reduced pressure in the enclosure formed by the sealant layer is less than approximately 400 mm Hg. In some embodiments, the self-created level of reduced pressure in the enclosure formed by the sealant layer is less than approximately 250 mm Hg. In some embodiments, the self-created level of reduced pressure in the enclosure formed by the sealant layer is less than approximately 125 mm Hg. In some embodiments, the self-created level of reduced pressure in the enclosure formed by the sealant layer is less than approximately 75 mm Hg. In some embodiments, the self-created level of reduced pressure in the enclosure formed by the sealant layer is less than approximately 50 mm Hg. In some embodiments, the self-created level of reduced pressure in the enclosure formed by the sealant layer is less than approximately 25 mm Hg. In some embodiments, the self-created level of reduced pressure in the enclosure formed by the sealant layer is less than approximately 10 mm Hg. In some embodiments of the device described herein, the sealant layer generally follows the perimeter of the area of tissue requiring therapy.

In some embodiments, the device is positioned on the patient and reduced pressure is applied to the area of tissue to be treated. In a further embodiment, the device may augment the level of reduced pressure already present underneath the sealant layer of the device by further expanding the volume underneath the sealant layer. The volume may be expanded either by adjusting the suction apparatus used to initially create the reduced pressure or by attaching a second suction apparatus to further expand the volume underneath the sealant layer.

The tissue therapy device can have alternative embodiments of the suction apparatus for creating reduced pressure within the wound dressing. In one embodiment, the suction apparatus is non-electrically powered. In some embodiments, the suction apparatus is manually operated in order to create suction. In one embodiment, the suction apparatus comprises a closed collection chamber with fixed walls in which a reciprocating piece alters the volume of the collection chamber. In one embodiment, the suction apparatus is a syringe. In a further embodiment, the plunger of the syringe serves as the reciprocating mechanism of the suction apparatus. The suction apparatus is engaged by drawing back the reciprocating mechanism in order to create a reduction in pressure. In another alternate embodiment, a handle attached to the reciprocating mechanism of the syringe is employed to draw back the reciprocating mechanism. The reciprocating mechanism may be drawn back by any suitable means known to one skilled in the art. The drawing back of the reciprocating mechanism in the suction apparatus enlarges the collection volume inside of the suction apparatus. The drawing back of the reciprocating mechanism expands the volume inside the suction apparatus (underneath the reciprocating mechanism) which is in fluid communication with the enclosure under the sealant layer of the wound dressing. The enclosure under the wound dressing and the space underneath the suction device chamber are de-facto one chamber with a fixed amount of air molecules. Once the reciprocating mechanism is drawn back, the volume of the enclosure increases and density of air molecules decreases. In another embodiment, the suction apparatus may be mechanically powered. In such an embodiment, the suction apparatus may be a mechanically powered vacuum pump.

In some embodiments, a sealant layer is provided. The sealant layer may be used to form a seal with the skin of the patient. In some embodiments, the seal is substantially airtight. Such a seal may be created around the perimeter of the area to be treated. In some embodiments, the seal is prefabricated into a fixed shape. In some embodiments, the fixed shape may be a circle, an oval, a square, a rectangle, a triangle, for example. In such an embodiment, the sealant layer may be shaped by the user to conform to the contours of the area to be treated.

In addition to self-creating reduced pressure, the suction apparatus of the tissue therapy device may also be adapted and configured to maintain a level of reduced pressure or a range of reduced pressures to be applied to the area of tissue to be treated. The level of reduced pressure may be maintained at a level anywhere between about 0 to about 760 mm Hg. In some embodiments, the device is configured to self-create reduced pressure without the use of electrical power. In a further embodiment, the device maintains the level of reduced pressure it self-creates, or a range of reduced pressures it self-creates. In some embodiments, the device maintains a level of reduced pressure between approximately 0 and approximately 760 mm Hg. In some embodiments the self-created level of reduced pressure in the enclosure formed by the sealant layer is maintained at more than approximately 10 mm Hg. In some embodiments, the self-created level of reduced pressure in the enclosure formed by the sealant layer is maintained at more than approximately 20 mm Hg. In some embodiments, the self-created level of reduced pressure in the enclosure formed by the sealant layer is maintained at more than approximately 50 mm Hg. In some embodiments, the self-created level of reduced pressure in the enclosure formed by the sealant layer is maintained at more than approximately 80 mm Hg. In some embodiments, the self-created level of reduced pressure in the enclosure formed by the sealant layer is maintained at more than approximately 100 mm Hg. In some embodiments, the self-created level of reduced pressure in the enclosure formed by the sealant layer is maintained at more than approximately 150 mm Hg. In some embodiments, the self-created level of reduced pressure in the enclosure formed by the sealant layer is maintained at more than approximately 200 mm Hg. In some embodiments, the self-created level of reduced pressure in the enclosure formed by the sealant layer is maintained at more than approximately 500 mm Hg. In some embodiments, the self-created level of reduced pressure in the enclosure formed by the sealant layer is maintained at more than approximately 700 mm Hg. In some embodiments, the self-created level of reduced pressure in the enclosure formed by the sealant layer is maintained at less than approximately 750 mm Hg. In some embodiments, the self-created level of reduced pressure in the enclosure formed by the sealant layer is maintained at less than approximately 700 mm Hg. In some embodiments, the self-created level of reduced pressure in the enclosure formed by the sealant layer is maintained at less than approximately 600 mm Hg. In some embodiments, the self-created level of reduced pressure in the enclosure formed by the sealant layer is maintained at less than approximately 400 mm Hg. In some embodiments, the self-created level of reduced pressure in the enclosure formed by the sealant layer is maintained at less than approximately 250 mm Hg. In some embodiments, the self-created level of reduced pressure in the enclosure formed by the sealant layer is maintained at less than approximately 125 mm Hg. In some embodiments, the self-created level of reduced pressure in the enclosure formed by the sealant layer is maintained at less than approximately 75 mm Hg. In some embodiments, the self-created level of reduced pressure in the enclosure formed by the sealant layer is maintained at less than approximately 50 mm Hg. In some embodiments, the self-created level of reduced pressure in the enclosure formed by the sealant layer is maintained at less than approximately 25 mm Hg. In some embodiments, the self-created level of reduced pressure in the enclosure formed by the sealant layer is maintained at less than approximately 10 mm Hg.

The level of reduced pressure may be applied and maintained by the reduced pressure tissue therapy device for short periods of time or for extended periods of time. In some embodiments, the reduced pressure may be applied and maintained for as short as approximately 30 minutes or for as long as over 4 weeks. In some embodiments, the reduced pressure is applied for longer than 30 minutes. In some embodiments the reduced pressure is applied for longer than 24 hours. In some embodiments, the reduced pressure is applied for longer than several days. In some embodiments, the reduced pressure is applied for longer than one week. In some embodiments, the reduced pressure is applied for longer than 4 weeks. In some embodiments, the device may incorporate an external suction apparatus if so desired.

The device can maintain the level of reduced pressure in several ways. In one embodiment, the device is engaged to create reduced pressure by engaging the non-electrical reciprocating mechanism located in the suction apparatus. In one embodiment, the resistance between the outside surfaces of the reciprocating mechanism and the inside surfaces of the suction apparatus are sufficient to maintain the level of reduced pressure underneath the sealant layer. In another embodiment, the suction apparatus is such that it further comprises a ratcheting mechanism. In one embodiment, the suction apparatus with ratcheting mechanism comprises a set of interlocking teeth integrated with the body of the suction apparatus and on sides of the reciprocating mechanism. The interlocking teeth resist or prevent the suction apparatus from losing its suction force by maintaining the position of the reciprocating mechanism in an extended position. This prevents or resists the shaft of the reciprocating mechanism from changing its position in response to the pressure inside the collection chamber. In another embodiment, the ratcheting system comprises a twist and lock mechanism which prevents the reciprocating mechanism from changing position in the suction apparatus.

In a further embodiment, the suction apparatus of the tissue therapy device may also serve as a collection chamber. The collection chamber includes a closed chamber, which may or may not be cylindrical in shape, in which a sliding or reciprocating piece or reciprocating mechanism may be manipulated to alter the volume of the chamber, thereby changing the density of the molecules located in the enclosure created by the sealant layer which is in fluid communication with the suction device. In some embodiments, the suction apparatus may serve a two-fold function. The suction apparatus may be used to create the reduced pressure underneath the sealant layer of the wound dressing. The suction apparatus may also be used to collect exudate or necrotic debris that is drawn up out of the wound.

In some embodiments, the suction apparatus and the wound dressing may be separate pieces. In an alternate embodiment, the suction apparatus and the wound dressing may be attached together. In such an embodiment, the suction device is connected to the tissue therapy device and together both pieces are considered to be a single device. In some embodiments the wound dressing has a compression gasket attached to it, which provides for at least one attachment point for a suction apparatus to the wound dressing. In some embodiments, the compression gasket is such that there is more than one attachment point. In some embodiments, a single suction apparatus is attached to the attachment point of the compression gasket of the wound dressing to create negative pressure. In an alternative embodiment, a second suction apparatus may be attached to the compression gasket at a second attachment point located on the compression gasket. This embodiment may be used in order to collect a larger volume of exudate. In some embodiments, the volume of the suction apparatus is between about 1 ml and about 1000 ml. In some embodiments, the volume of the suction apparatus may be about 1 ml. In some embodiments, the volume of the suction apparatus may be about 5 ml. In some embodiment, the suction apparatus may be about 10 ml. In some embodiments, the suction apparatus may be about 20 ml. In some embodiments, the suction apparatus may be about 30 ml. In some embodiments, the suction apparatus may be about 50 ml. In some embodiments, the suction apparatus may be about 100 ml. In some embodiments, the suction apparatus may be about 500 ml. In some embodiments the suction apparatus may be about 1000 ml or more.

In some embodiments, the suction apparatus may be disconnected from the wound dressing. For example, the suction apparatus may be disconnected from the wound dressing in order to empty the suction apparatus. In some specific examples, emptying the suction apparatus is performed when the amount of exudate in the suction apparatus reduces the effectiveness of the suction on the wound. In one embodiment, once the suction apparatus has been emptied, it can then be reconnected to the wound dressing. In an alternate embodiment, the suction apparatus is disconnected from the wound dressing and discarded and a new suction apparatus is attached to the wound dressing. In some embodiments, the suction apparatus replacing the discarded suction apparatus is the same kind of suction apparatus as the discarded suction apparatus. In other embodiments, the suction apparatus replacing the discarded suction apparatus is a different size or kind of suction apparatus than the discarded suction apparatus. For example, in some embodiments, the replacement suction apparatus may be smaller than the discarded suction apparatus. A smaller replacement suction apparatus may be used as the fluid and/or exudate secreted from a wound decreases over time, for example. In other examples, a larger suction apparatus may be provided during non-ambulatory periods (e.g. bedtime), while a smaller suction apparatus is provided during ambulatory periods. In some embodiments, the suction apparatus may be detached from the wound dressing while the reduced pressure created by the suction apparatus is maintained on the wound, even after the suction apparatus has been detached.

In some of the embodiments, the tissue therapy device is designed such that the device resists or prevents the backflow of exudate from the collection chamber of the suction device to the area of tissue to which therapy is applied. In some embodiments, the back flow is resisted or prevented by the inherent resistance of the suction apparatus. The inherent resistance may include but is not limited to the frictional resistance of the plunger, for example. In some embodiments, the tissue therapy device may include a one-way flow mechanism to prevent exudate from returning to the area of tissue requiring therapy or to the wound surface. In some embodiments, the one way flow mechanism may be a valve. In some embodiments, a filter or an absorbent structure, for example, may be provided to reduce redistribution of exudates, back to the treatment area.

In some embodiments, the tissue therapy device may be configured as a portable device that may be worn or carried by the patient or the patient's ambulation assistance device (e.g. wheelchair or walker). In other embodiments, the tissue therapy device is designed such that it may be secured to the patient (e.g. limb or torso). In some embodiments, the sealant layer is preferably adhered directly to the skin of the patient. The suction apparatus can then be put in fluid communication with the enclosure formed by the sealant layer. The sealant layer and the suction apparatus may be secured to the patient and carried around. In some of the embodiments mentioned, the tissue therapy device may be attached to the patient by any suitable means for securing the device to the patient. In some embodiments, the device is secured through the use of adhesive tape. In other embodiments, the device may be secured to the patient through the use of a strap, a hook-and-loop or a touch fastener such as VELCRO®, an elastic band, a cuff, an adhesive bandage, or any other suitable mechanisms for securing the device to the patient. In some embodiments, the securing mechanism may be configured with a holster or other type of pocket structure to hold the suction apparatus. In some embodiments, the greater surface area of a cuff may reduce the risk of causing focal pressure points or regions as a result of securing the tissue therapy device. In some embodiments, a cuff having a longitudinal length of at least about half of its diameter is provided. In other embodiments, the cuff has a longitudinal length of at least about equal to its diameter. In other embodiments, the cuff may have a longitudinal length of at least about 1.2 times its diameter, sometimes at least about 1.5 times its diameter, and other times at least about 2 times or 3 times its diameter. In some embodiments, the securing device may comprise a band or cuff that is also be configured to apply an amount of pressure to the tissue surrounding the treatment area. This may be beneficial, for example, when the treatment area is a wound caused by venous stasis. The amount of pressure exerted by the securing device may be about 40 mm Hg or less, sometimes about 20 mm Hg or less and other times about 10 mm Hg or less, or about 6 mm Hg or less.

In one embodiment, the suction apparatus may be attached directly to the sealant layer by an attachment fitting. In another embodiment, fluid communication between the suction apparatus and the enclosure formed by the sealant layer may be provided by an extension tube. In this embodiment, the extension tube may be used to facilitate the attachment of the suction apparatus to the patient by permitting distance between the suction apparatus and the wound dressing and thereby allowing for placement of the suction apparatus where convenient.

In some embodiments of the wound therapy device described herein, a safety valve is included in the tissue therapy device. The safety valve may be a pressure-activated bleed valve that opens when excessively high negative pressure builds up in the device. In some embodiments, the safety valve opens in response to a set level of pressure.

In one embodiment of the tissue therapy device, the tissue therapy device may be used to provide therapy to a wound on the surface of the patient. In such an embodiment, in addition to the suction apparatus and the sealant layer, the tissue therapy device may comprise a contact layer. In some embodiments where a contact layer is used, the contact layer is placed in contact with a wound and not in contact with any surrounding tissue. In some embodiments, the contact layer is placed in contact with the wound and is in contact with the surrounding tissue. The sealant layer is then placed over the contact layer. The sealant layer creates a seal around the perimeter of the wound. In some embodiments the seal is airtight. The sealant layer then creates a seal with the surface of the skin by adhering to the surface surrounding the wound. In some embodiments, the sealant layer is integrated with the contact layer.

In some embodiments, the contact layer and the sealant layer may be integrated into the same structure. The contact layer may be configured to provide fluid communication between the suction apparatus and the wound surface. In some embodiments, any two of the sealant layer, the suction apparatus, or the contact layer may be integrated into the same structure while the third structure remains an independent separate structure. In some embodiments, the contact layer and the sealant layer are integrated together while the suction apparatus is a separate structure. In some embodiments, the contact layer and the suction apparatus are integrated together, while the sealant layer is a separate structure. In some embodiments, the sealant layer and the suction apparatus are integrated together while the contact layer is a separate structure.

In an embodiment comprising a contact layer, the contact layer may be any suitable material known in the art to serve as a protective layer to the wound itself. Examples of materials that may be used include, but are not limited to, gauze, foam, cotton, particulate material, and any other suitable protective material that is known in the art. In some embodiments a layer of a nonreactive or biocompatible material is placed on the wound surface prior to the contact layer being placed on the wound surface. The material may made from any suitable fluoropolymer, such as polytetrafluoroethylene (PTFE), perfluoroalkoxy polymer resin (PFA), fluoroinated ethylene-propylene (FEP), polyethylenetetrafluoroethylene (ETFE), polyvinylfluoride (PVF), polyethylenechlorotrifluoroethylene (ECTFE), polyvinylidene fluoride (PVDF), polychlorotrifluoroethylene (PCTFE), or any other suitable nonreactive or biocompatible material or fluoropolymer known in the art. In some embodiments, the nonreactive or biocompatible material resists or prevents the wound from adhering to the contact layer.

In some embodiments, the contact layer of the tissue therapy device comprises a stacked mesh matrix. In some embodiments, the stacked mesh matrix comprises at least two mesh matrix sheets. In some embodiments, the stacked mesh matrix comprises multiple mesh matrix sheets. The stacked mesh matrix may be adapted and configured to provide fluid communication between the suction apparatus and an area of tissue which requires treatment.

In some embodiments, the contact layer of the tissue therapy device comprises an adjustable micro-particles pouch. The micro-particles and the pouch may be adapted and configured to provide fluid communication between the suction apparatus and the area of tissue requiring treatment. In some embodiments the micro-particles are made from a polymer material. In some embodiments the pouch contains at least two particles. In some embodiments the pouch volume can be adjusted by adding or subtracting micro-particles from the pouch without disturbing the integrity of the pouch.

In one embodiment, the contact layer may be prefabricated to a specific size and shape. In another embodiment, the contact layer may be prefabricated to a specific size and shape and then cut so that the prefabricated contact layer conforms to the shape or size of the wound.

In an embodiment where a stacked mesh matrix is used as the contact layer, the stacked mesh matrix comprises a series of thin filaments. In some embodiments, the filaments are made from a polymer material. The filaments of the stacked mesh matrix may be oriented such that the filaments lie perpendicular to one another. In some embodiments the filaments are randomly oriented. In some embodiments, the filaments are between approximately 0.001 mm to approximately 10 mm thick. In some embodiments, the filaments are more than approximately 0.01 mm thick. In some embodiments the filaments are more than approximately 0.05 mm thick. In some embodiments, the filaments are more than approximately 0.1 mm thick. In some embodiments the filaments are more than approximately 0.5 mm thick. In some embodiments, the filaments are more than approximately 1 mm thick. In some embodiments the filaments are more than approximately 2.5 mm thick. In some embodiments, the filaments are approximately more 5 mm thick. In some embodiments, the filaments are approximately more than 7.5 mm thick. In some embodiments, the filaments are approximately more than 10 mm thick. In some embodiments, the filaments are less than approximately 10 mm thick. In some embodiments, the filaments are less than approximately 5 mm thick. In some embodiments the filaments are less than approximately 1 mm thick. In some embodiments, the filaments are less than approximately 0.05 mm thick. In some embodiments the filaments are less than approximately 0.01 mm thick. In some embodiments the filaments are less than approximately 0.005 mm thick. In some embodiments, the filaments are less than 0.001 mm thick. In some embodiments, all the filaments throughout the stacked mesh matrix are of a uniform thickness. In other embodiments, the filament thickness is variable throughout the stacked mesh matrix.

In some embodiments of the wound therapy device, a mesh matrix sheet comprises filaments that are spaced between approximately 1 mm to 15 mm apart. In some embodiments the filaments are spaced more than about 1 mm apart. In some embodiments the filaments are spaced more than about 2 mm apart. In some embodiments the filaments are spaced about 4 mm apart. In some embodiments the filaments are spaced about 6 mm apart. In some embodiments the filaments are spaced about 8 mm apart. In some embodiments the filaments are space about 10 mm apart. In some embodiments the filaments are spaced about 12 mm apart. In some embodiments the filaments are spaced about 15 mm apart. In other embodiments the filaments are spaced between approximately 1 mm to approximately 5 mm apart. In some embodiments the filaments are spaced between approximately 5 mm to 10 mm apart. In some embodiments the filaments are spaced approximately 10 mm to 15 mm apart. In some embodiments, the filaments are spaced uniformly throughout the stacked mesh matrix. In other embodiments, the filaments are variably spaced throughout the stacked mesh matrix.

The stacked mesh matrix of the wound dressing may be designed to include other features. In some embodiments of the stacked mesh matrix, the stacked mesh matrix can deliver biologics to the wound through the filaments of a delivery mesh. In one embodiment of the stacked mesh matrix, the filaments of the delivery mesh are solid filaments soaked in a solution containing biologics or therapeutics. In an alternative embodiment of the stacked mesh matrix, the filaments of the delivery mesh are hollow. Examples of biologics to facilitate wound healing include, but are not limited to, antibiotics and growth factors. In other embodiments of the stacked mesh matrix, the delivery mesh may be used to irrigate the wound. In some embodiments where a delivery mesh is used, a separate external fluid source may be connected to the delivery mesh.

In another embodiment, the stacked mesh matrix comprises a single mesh matrix sheet. In another embodiment, the stacked mesh matrix comprises more than two or multiple mesh matrix sheets to create a multi-layered dressing. In this embodiment, the stacked mesh matrix may be separated to a desired thickness based on the thickness of the wound. In a further embodiment, the stacked mesh matrix may include a delivery mesh layer. In some embodiments, the delivery mesh is located on the bottom of the stacked mesh matrix. In some embodiments, the delivery mesh is located at the top of the stacked mesh matrix. In some embodiments, the delivery mesh is located anywhere but at the top or bottom of the stacked mesh matrix.

In some embodiments, a method for applying reduced pressure therapy to an area of tissue is provided, comprising creating a sealed enclosure around an area of tissue to be treated by affixing a sealant layer to a surface of a patient. Reduced pressure is then self-created underneath the sealant layer by expanding a volume of the enclosure using a suction apparatus in fluid communication with the enclosure created by the sealant layer. In some embodiments the method uses a closed reduced pressure therapy system, comprising a sealant layer and a suction apparatus. In some embodiments, the sealed enclosure is air-tight. In some embodiments, the method further comprises providing a contact layer on the wound surface before the sealant layer is affixed to the surface of the patient. In some embodiments of the method described herein, the method further comprises applying a protective layer around the area of the tissue to be treated before creating the sealed enclosure. In some embodiments the method further comprises applying a hydrocolloid to the area of tissue to be treated. In some embodiments of the method described herein, the method further comprises creating reduced pressure with an external suction apparatus.

In some embodiments, a method of treating a wound using a reduced pressure therapy device is provided, comprising creating a sealed enclosure between a sealant layer of a wound dressing and the surface of a patient and applying self-created reduced pressure to a wound by forcefully expanding a volume of air molecules enclosed in the sealed enclosure. In some embodiments, the method uses a closed reduced pressure therapy system. In some embodiments, the wound to be treated is selected from an acute wound, a partial- or full-thickness burn, a surgically created wound or surgical dehiscence, neuropathic (diabetic) wounds, venous or arterial insufficiency ulcers, traumatic wounds, and pressure ulcers, and any other wound or damaged tissue for which the application of reduced pressure therapy is suitable.

In another embodiments, a method of treating an area of damaged tissue using reduced pressure tissue therapy is provided, comprising positioning a reduced pressure tissue therapy device over an area of tissue to be treated, where the reduced pressure tissue therapy device comprises a sealant layer and a suction apparatus, and reducing the level of pressure in a volume of air located under the sealant layer by engaging the suction apparatus, where the suction apparatus self-creates the reduction in pressure by forcefully expanding the volume of air. In some embodiments, the sealant layer and the suction apparatus form a closed reduced tissue therapy system. In some embodiments of the method described herein, the method further comprises decreasing the density of air molecules under the sealant layer to create reduced pressure.

FIG. 1A illustrates one embodiment of a tissue therapy device 100. FIG. 1A shows a wound dressing 102 and a suction apparatus 104. The wound dressing 102 comprises a sealant layer 108. In some embodiments, the wound dressing further comprises a contact layer. In some embodiments, the contact layer provides fluid communication between the wound and the suction apparatus. The contact layer may comprise a foam, a mesh, a gauze, a sponge, a particulate matter, a stacked mesh matrix, or any other suitable biocompatible material or biocompatible porous structure, or any combination thereof. The contact layer may be placed in contact with the wound surface. Once positioned, the contact layer is then covered by the sealant layer 108. In some embodiments the contact layer is placed separately on the wound followed by the placement of the sealant layer. In some embodiments, the contact layer and the sealant layer are integrated together to streamline application of the wound dressing. The sealant layer may be affixed to the surface of the patient surrounding the wound by any suitable adhesive means known to one skilled in the art. Such adhesives may include, but are not limited to, tape, glue, or a suitable biocompatible adhesive product.

Further depicted in FIG. 1A is a suction apparatus 104. In some embodiments, the suction apparatus 104 self-creates reduced pressure underneath the sealant layer 108 of the wound dressing 102. The suction apparatus 104 may also be used to collect any exudate or debris drawn up from the wound. In some embodiments, the suction apparatus 104 comprises a collection chamber 120 having rigid sides 136 and a hollow interior. A sliding seal or fitted reciprocating mechanism 138 seals against the interior sides 140 of the collection chamber 120. When in use, the end of the reciprocating mechanism 142 may be engaged thereby increasing or decreasing the volume of the collection chamber 120. Engaging the end of the reciprocating mechanism 142 also creates reduced pressure within the wound dressing.

The suction apparatus 104 of the wound therapy device 100 may be connected to the wound dressing 102 by way of a compression fitting 122. The compression fitting 122 provides a mechanism or structure for attaching the suction apparatus 104 to the sealant layer 108. In some embodiments, the compression fitting 122 may comprise two or more components. For example, FIG. 1A shows one of two attachment pieces 124 of the compression fitting 122 of the tissue therapy device 100. The attachment pieces of the compression fitting 122 may be configured to sandwich the sealant layer 108 such that one attachment piece 124 is underneath the sealant layer 108 and one attachment piece is above the sealant layer 108. The two attachment pieces are then secured together to hold the sealant layer between the attachment pieces. In some embodiments, the attachment pieces are secured together with screws 126 as shown in FIG. 1A. In some embodiments the attachment pieces are secured together with an adhesive. Other securing mechanisms include but are not limited to mechanical interfits including snapfits, frictional interfits, welding, heat melding, and the like. In some embodiments the attachment piece 124 is made from acrylic. In some embodiments the attachment piece is made from, but not limited to, silicon, metal, or polymer materials, plastic, or any other suitable biocompatible material. In some embodiments the device has two attachment pieces. In some embodiments, the attachment piece is a single piece, such as a single piece of molded silicon. An aperture 125 in the middle of the attachment pieces allows for communication between the wound and the suction apparatus.

The suction apparatus 104 may be attached to the attachment piece 124 of the compression fitting 122 using a compression gasket 128. In some embodiments, the compression gasket 128 may be inserted into the aperture 125 in the middle of the attachment pieces 124. The suction apparatus 104 is attached to the compression gasket 128 by inserting the neck of the suction apparatus 104 into a stem 132 of the compression gasket 128. In one embodiment the suction apparatus 104 may be attached to the compression gasket 128 by inserting the suction apparatus 104 into the compression gasket 128. Alternatively, in other embodiments, the suction apparatus 104 may be attached to the compression gasket 128 by screwing the suction apparatus 104 into the stem 132 of the compression gasket 128. In some of the previously described embodiments, the suction apparatus 104 may be easily detached and reattached if desired or required.

The tissue therapy device, as described herein, comprises a compression gasket 128 equipped with at least one stem 132 for attaching the suction apparatus. In some embodiments, the compression gasket may have a second connector 133 as shown in FIG. 1A. In such an embodiment, the connector 133 may be used for attaching a second suction apparatus. In an alternate embodiment, the connector 133 may be used to attach a separate external collection chamber.

In some embodiments, the suction opening in the tissue dressing may be pre-formed, but in some other embodiments, the suction opening may be formed at the point-of-use. In some embodiments, the dressing may comprise perforations, regions of reduced thickness, or other structural features that may be provided to facilitate formation of a suction opening. In some embodiments, more than one suction opening may be formed in the dressing, and more than one suction aperture forming structure may optionally provided.

In some embodiments, the wound therapy device incorporates a three-way valve 134. In one position, the valve allows exudate to be drawn up from the wound into the suction apparatus. In a second position the valve closes the communication between the wound dressing and the suction apparatus such that reduced pressure is maintained during emptying or replacement of the suction apparatus. In a third position, the valve allows fluid communication between the suction apparatus and an external collection chamber, while preventing exudate from returning to the wound surface.

Figure 1B:
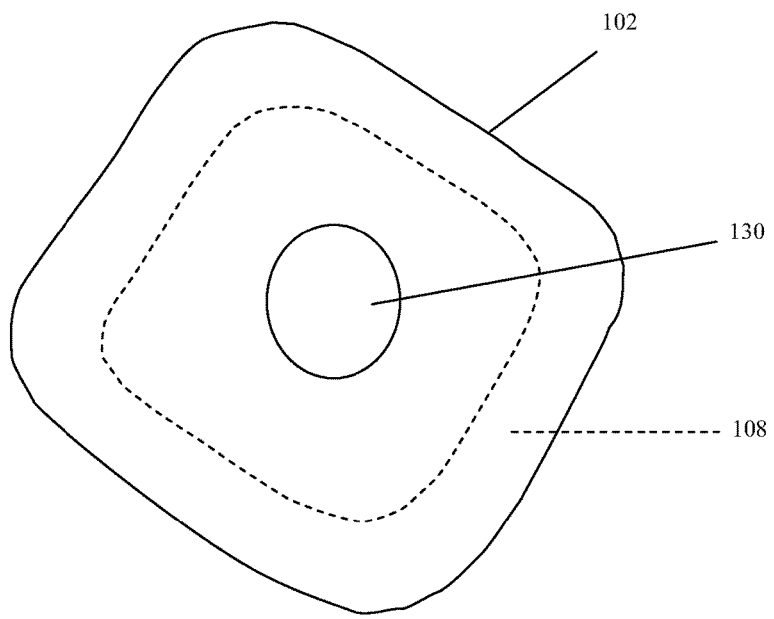

FIG. 1B shows an illustration of one embodiment of a wound dressing 102 of the tissue therapy device. The sealant layer 108 of the wound dressing comes in contact with the surface of the patient around the perimeter of the wound. FIG. 1B further illustrates a hole 130 in the middle of the wound dressing 102. One attachment piece is positioned on one side of the hole and another attachment piece is positioned on the other side of the hole as shown in FIG. 1A. The compression gasket is then attached to the attachment pieces as shown in FIG. 1A.

Figure 11A:
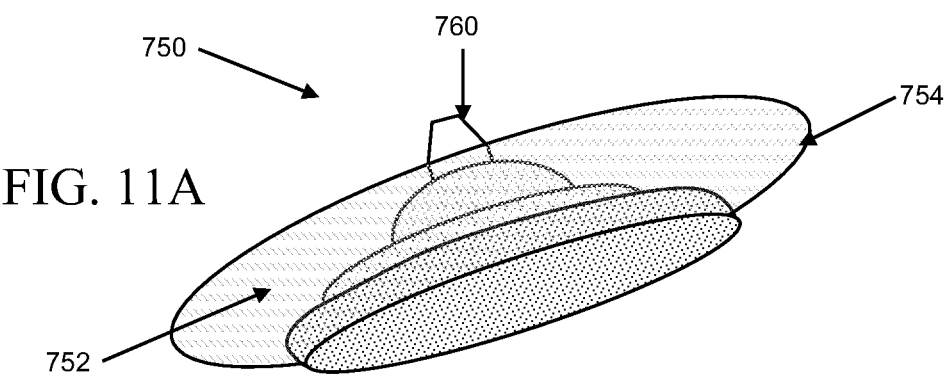
FIG. 11A is an inferior perspective view of another embodiment of a cover layer and a contact layer.
Figure 11B:
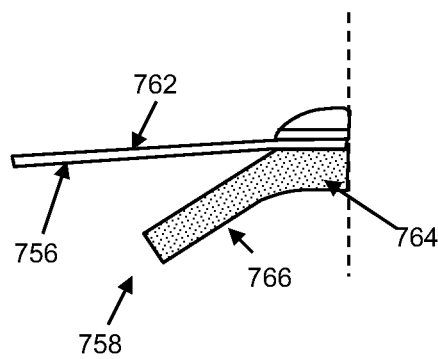
FIG. 11B is a cross-sectional view of the cover layer and the contact layer of FIG. 11A.

FIG. 11A depicts another embodiment of a wound dressing 750. In this particular embodiment, the wound dressing 750 comprises a sealing film 752 with an adhesive region 754 located along the perimeter of the sealing film 752. Located on the inner surface 756 of the sealing film 752 is a contact layer 758, while a suction connector 760 is located on the outer surface 762 of the sealing film 752. The contact layer 758 depicted in FIGS. 11A and 11B comprises a sponge material, but other contact layer materials or combinations of materials may also be used. As shown in FIG. 11B, the contact layer 758 has a central portion 764 that is in contact with the inner surface 756 of the sealing film 752, and a perimeter portion 766 that is unattached from the inner surface 762 of the sealing film 752. In some embodiments, the central portion 764 of the contact layer 758 is glued or otherwise attached to the inner surface 762 of the sealing film 752, while in other embodiments the contact layer 758 is connected to the suction connector 760 without any specific attachment to the sealing film 752. In some of these embodiments, the contact layer 758 may be substantially unattached to the sealing film 752, while in other embodiments, the rigidity or geometry of the contact layer 758 maintains a significant portion of the contact layer 758 against the sealing film 752 without any adhesive or other securing mechanisms. In some embodiments, the contact layer 758 is pre-formed with a generally concave shape that biases the perimeter portion 766 of the contact layer 758 away from the sealing film 752. In other embodiments, however, the contact layer 758 may be configured with a generally convex or any other configuration. In some embodiments, the contact layer 758 is pre-formed with a generally planar configuration, but is sufficiently flexible such that when dry or when wet, gravity is sufficient to flex the perimeter portion 766 of the contact layer 758 away from sealing film 752. In some embodiments, the surface 768 of the perimeter portion 766 adjacent the sealing film 752 may be provided with a non-stick surface to resist adhesion to the adhesive region 754 of the sealing film 752.

Figure 2:
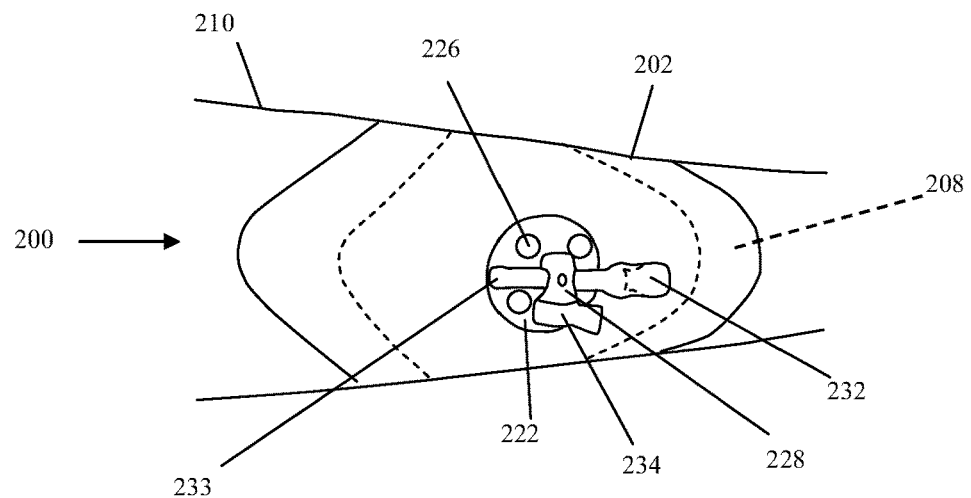
FIG. 2 illustrates one embodiment of a top view of a wound dressing and stem to which the suction apparatus is attached in position on a patient.

Provided herein is a device for tissue therapy that delivers reduced pressure to an area of tissue. The tissue therapy device 200 is used by applying the wound dressing 202 of the device 200 to a patient 210 over a wound. The distal side of the sealant layer 208 together with the compression fitting 222 as placed on the patient is seen in FIG. 2. In some embodiments, the attachment pieces are attached to the sealant layer prior to placing the wound dressing on the patient. In some embodiments, the attachment pieces are attached to the sealant layer after the sealant layer has been positioned on the patient. In some embodiments, as seen in FIG. 2, the attachment pieces are secured together using screws 226. In some embodiments, the attachment pieces are secured together using any suitable means available to fasten the attachment pieces together. In some embodiments the compression gasket is already integrated with the attachment pieces. In one aspect, a three-way valve 234 is integrated with the compression fitting 222 as shown in FIG. 2. The three-way valve 234 may be used in any means previously described. The three-way valve 234 may be set to the open position for exudate to flow into the collection chamber of the suction apparatus. The suction apparatus is then connected to the stem 232 of the compression gasket 228. In some embodiments, an external additional suction apparatus may be attached to the device via a second connection stem 233. In some embodiments, an external collection chamber may be attached to the device by attaching the external collection chamber to the second connection stem 233.

Figure 3:
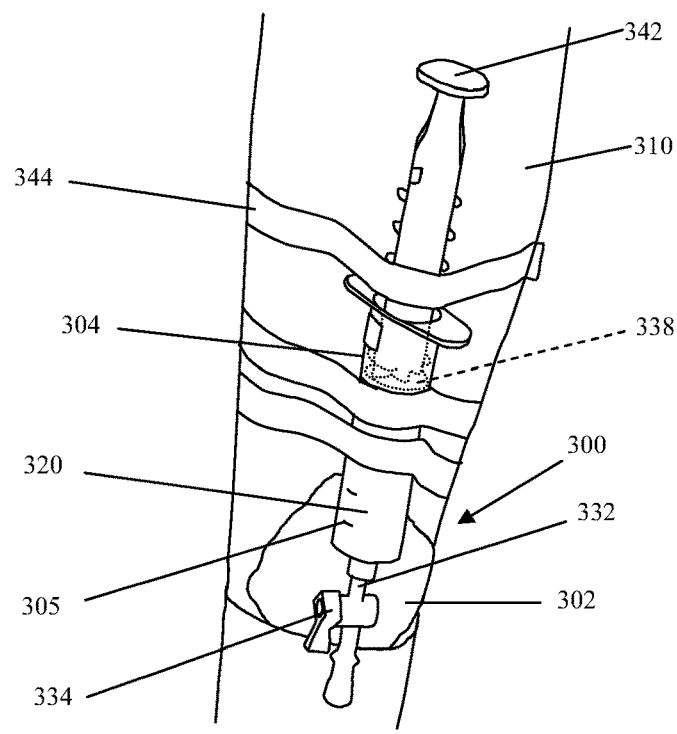
FIG. 3 is an illustration of a distal view of a reduced pressure tissue therapy device in position on a patient.

Also provided herein is a reduced pressure tissue therapy device 300 wherein the tissue therapy device is portable. The portability of the device allows the patient to remain mobile during use. In one embodiment, the wound dressing 302 is placed over the wound of the patient. FIG. 3 shows a patient 310 having a wound in which the tissue therapy device 300 has been placed over the wound. In some embodiments, after the wound dressing 302 has been placed over the wound, a suction apparatus 304 is attached to the wound dressing by the stem 332 on the compression fitting. In some embodiments, the suction apparatus is already attached to the wound dressing. Reduced pressure may be created by engaging the end 342 of the reciprocating mechanism 338 of the suction apparatus 304. In some embodiments, the suction apparatus 304 is unmarked; the suction apparatus has no markings to identify different strengths of, or settings corresponding to, levels of reduced pressure. In some embodiments, the suction apparatus 304 is marked with markings 305, as shown in FIG. 3, indicating different positions for the reciprocating mechanism to be drawn back to, creating different set levels of negative pressure as shown in FIG. 3. Exudate drawn from the wound is drawn into the collection chamber 320 when the three-way valve 334 is opened. In some embodiments, as shown in FIG. 3, the collection chamber 320 is the same as the suction apparatus 304.

After the wound dressing has been positioned on a patient 310 as shown in FIG. 3, the suction apparatus 304 may be secured to the patient 310 by any means suitable for adhering the device to the patient 310. In one aspect, the suction apparatus 304 is adhered to the patient with tape 344, as shown in FIG. 3. In alternate aspects, the suction apparatus is secured to a patient, with elastic bands, VELCRO® straps, adhesive bandages, gauze, or cloth strips, or any other suitable means for securing the suction apparatus to the patient.

Figure 4:
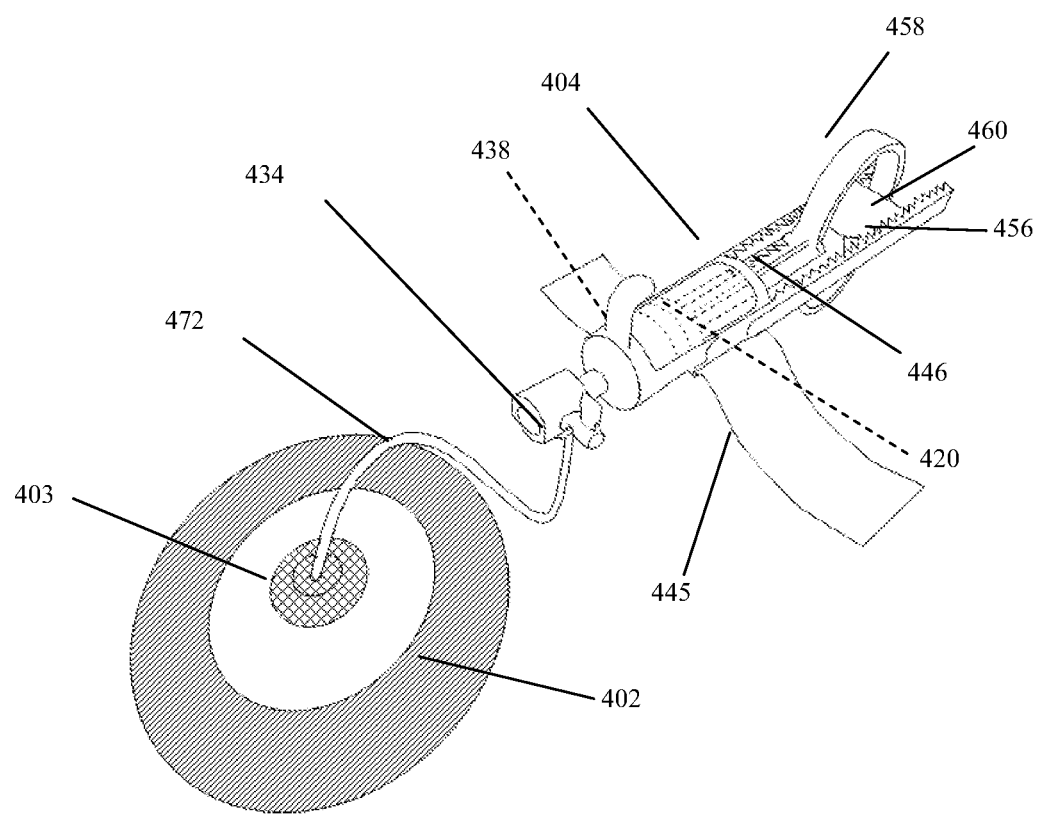
FIG. 4 is one embodiment of a top perspective of a reduced pressure tissue therapy device in which the suction apparatus is integrated together with a wound dressing.

In yet another embodiment of the tissue therapy device, the suction apparatus 404 comprises a ratcheting mechanism. In such an embodiment, the reciprocating mechanism 438 of the suction apparatus 404 is engaged using a handle 458, as shown in FIG. 4. In some embodiments, the reciprocating mechanism 438 is drawn back to create reduced pressure and the reduced pressure is maintained using resistance between the reciprocating mechanism and the interior walls of the syringe. In some embodiments, the reciprocating mechanism 438 is engaged to create reduced pressure and the reduced pressure is maintained by holding the reciprocating mechanism 438 in the position to which it is drawn back to using interlocking teeth 460 on the shaft 446 and the body 456 of the suction apparatus 404, as shown in FIG. 4. In such an embodiment, the reciprocating mechanism 438 is drawn back to the desired position and the teeth 460 on the shaft 446 and the body 456 of the suction apparatus may interlock to hold the reciprocating mechanism in place. FIG. 4 also shows a means for securing the suction apparatus to the patient, in the form of a strap 445 integrated into the body 456 of the suction apparatus 404.

In other embodiments, other configurations for maintaining the position of the sliding seal or reciprocating mechanism may be used. For example, in some embodiments, a helical threaded interface may be provided between the actuator (e.g. plunger) and the suction chamber. To provide suction, the actuator may be rotated to move the sliding seal or reciprocating mechanism and to generate a reduced pressure. In some embodiments, the helical threaded interface may be located on an internal surface of the suction chamber and an outer surface of the actuator. In other embodiments, the threaded interface may be located on the outer surface of the suction chamber and an inner surface of an interface member coupled to the actuator or plunger. In still other embodiments, a clamp or an interference structure, such as a retaining pin, may be used to maintain the position of the sliding seal or reciprocating mechanism.

Figure 13:
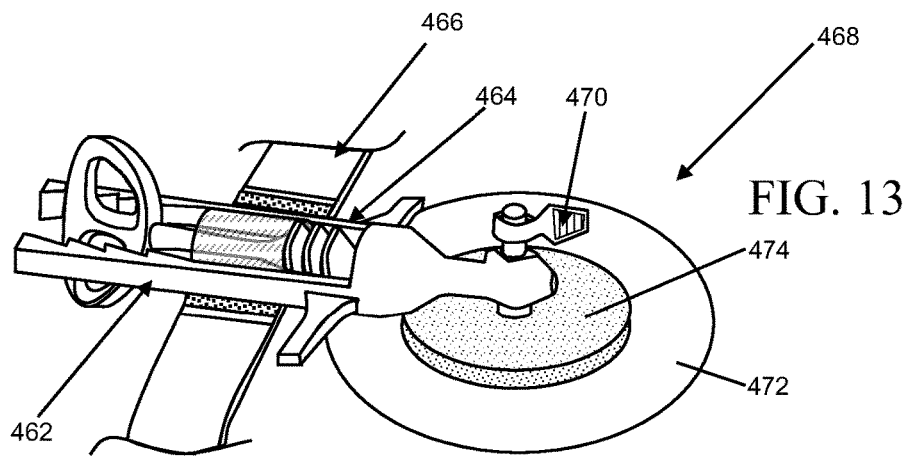
FIG. 13 is a perspective view of another embodiment of a reduced pressure tissue therapy device.

In some embodiments, the suction apparatus is attached directly to the wound dressing, as shown in FIG. 1A. In one particular example illustrated in FIG. 13, a suction apparatus 462 with a ratcheting assembly 464 and a securing strap 466 is coupled to a wound dressing 468 using a valve 470. In this particular example, the wound dressing 468 comprising a sealing layer 472 and a foam contact layer 474, but in other embodiments, a different contact layer material may be used. Other examples of contact layer materials are disclosed elsewhere herein. The sealing layer 472 may comprise any of a variety of materials, including but not limited to a polyethylene or polyurethane, for example. The sealing layer 472 may also include any of a variety of other components or coatings, including an acrylate polymer as included in TEGADERM® polyethylene dressing.

In an alternative embodiment, the suction apparatus 404 is attached to a wound dressing by a tube 472, as shown in FIG. 4. In such an embodiment, one end of a tube 472 is attached to an outlet port 403 of the wound dressing 402. The other end of the tube 472 is then attached to the suction apparatus 404 by a three-way valve 434. In one position, the three-way valve 434 allows exudate to be drawn up from the wound into the collection chamber 420. In a second position the three-way valve 434 closes the communication between the wound dressing and the suction apparatus such that negative pressure is maintained during emptying or replacement of the suction apparatus. In a third position, the three-way valve allows fluid communication between the suction apparatus 404 and an external collection chamber, while preventing exudate from returning to the wound. In some embodiments, use of a flexible tube permits the placement of the suction apparatus at a different location from the sealing layer of the tissue dressing. This may be beneficial, for example, by securing the suction apparatus in at a distance from a treatment location with pre-existing vascular compromise which may be further compromised by a securing strap or band of the suction apparatus.

In one embodiment, the wound dressing and suction apparatus may be placed directly over the wound on the patient without any preparation of the patient and a seal is created between the sealant layer and the skin of the patient.

In some embodiments, a contact layer is positioned on the wound before the sealant layer is placed over the wound. In some embodiments, the contact is placed on the wound as a separate structure after being trimmed to accommodate the shape of the wound. In such an embodiment, the contact layer is in contact only with the wound surface and not in contact with any area surrounding the wound. In some embodiments, the contact layer is in contact with the tissue surrounding the wound. In some embodiments of the wound dressing, the contact layer is integrated into the sealant layer. In such an embodiment, the edges of the contact layer are not attached to the sealant layer and may be trimmed to accommodate the shape of the wound.

In one embodiment of the wound therapy device described herein, the wound dressing and vacuum chamber manifold is placed directly over the wound on the patient without any preparation of the patient and a seal is created between the sealant layer of the wound dressing and the skin of the patient. In this embodiment, when the wound dressing is removed from the skin of the patient when the wound dressing has to be changed, the seal is broken and a new seal is formed has to be formed between the skin and the new wound dressing.

In another embodiment of the device described herein, before the wound dressing is placed on the skin of a patient, a protective layer 574 is placed on the skin of the patient before the sealant layer of the wound dressing is put in contact with the skin of the patient, as shown in FIG. 5A. In one embodiment, the protective layer is adhered to the skin of the patient using any suitable means for adhering the protective layer to the patient. In some embodiments, the protective layer may include a pressure adhesive layer. In some embodiments, the protective layer is prefabricated to a specified size or shape. In this embodiment, a protective layer is chosen such that is it larger than the size of the wound so that it can surround the perimeter of the wound. In some embodiments, the protective layer is adjusted to the size of the wound by a clinician. In this embodiment, the protective layer 574 may be cut by a clinician to mimic or generally track the shape or size of the wound, such that the protective layer follows the perimeter of the wound. In some embodiments, the protective layer is smaller than the size of the wound. FIGS. 5A and 5B show the protective layer 574 of FIG. 5A sized to fit the wound 590 shown in FIG. 5B. Once the protective layer is cut to the desired size or shape, the protective layer is placed on skin surface surrounding the wound 590, as shown in FIG. 5C. The protective layer 574 may comprise any of a variety of materials, including a polyurethane foam such as DUODERM®. Once the protective layer has been adhered to the skin of the patient, the sealant layer of the wound dressing is positioned in contact with the protective layer. A seal is formed between the sealant layer of the wound dressing and the protective layer. In some embodiments, the seal formed is airtight. In some embodiments where a protective layer is used, the protective layer serves to protect the edges of the wound from maceration, decrease the pain and skin trauma resulting from dressing change, and to form a strong seal between the dressing and the skin. In such an embodiment, the sealant layer and protective layer provide a reliable seal for delivering reduced pressure tissue therapy.

In some embodiments, the protective layer may comprise an annular seal that may be placed around the wound area, rather than over the dressing. The dressing may be configured that could fit within the seal using a screw-in or a snap-in mechanism, for example. When the dressing is changed, the annular seal may remain fixed to the wound or treatment area while the dressing is replaced. In some embodiments, the dressing may be attached to the seal around a central region of the seal while the edges of the dressing are generally not attached to the seal. In some of these embodiments, the dressing may be trimmed to generally accommodate the shape of the wound.

Figure 6:
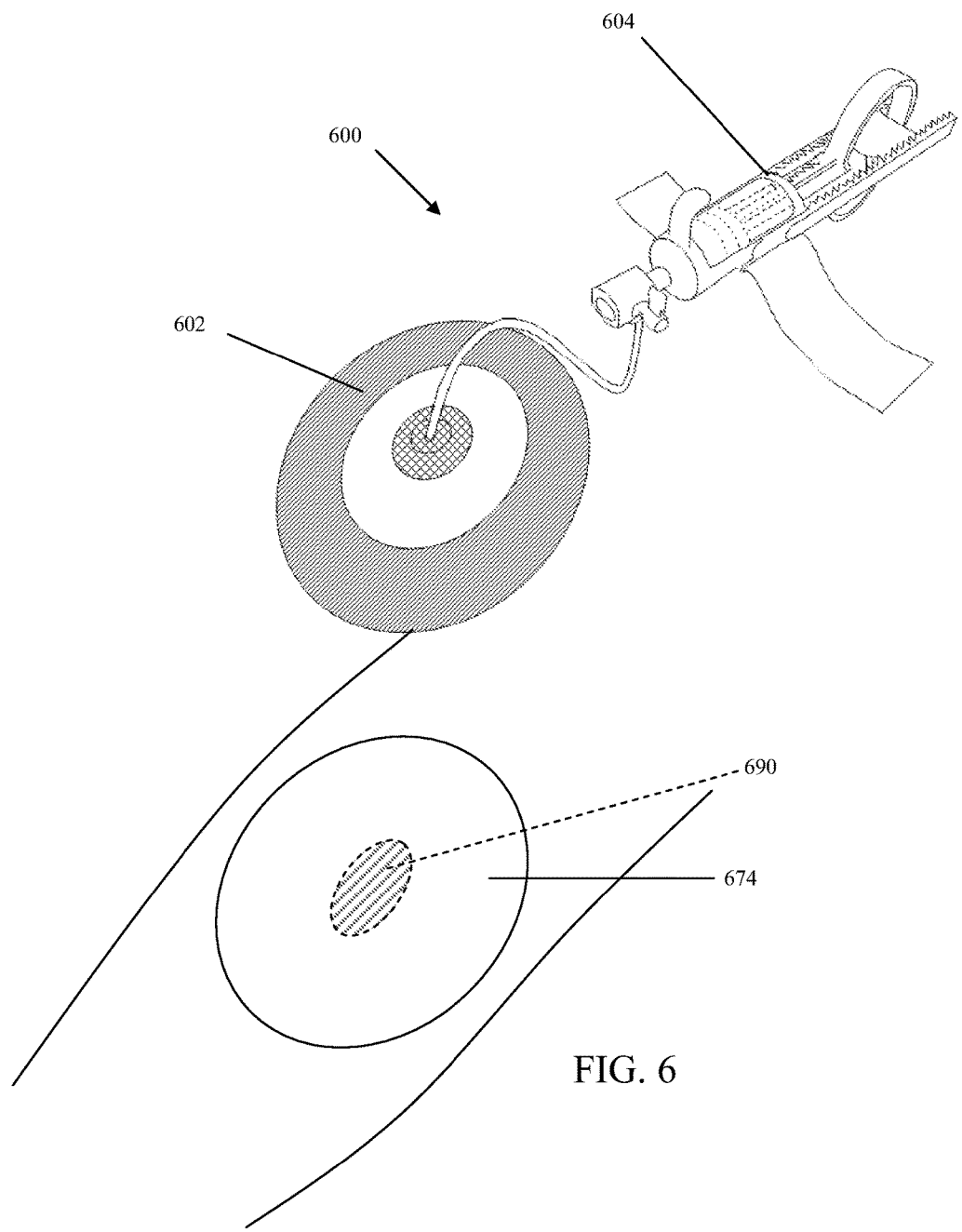
FIG. 6 is one embodiment an illustration of the wound dressing of FIG. 5 cut to the size of a wound and further illustrating how the wound dressing and suction apparatus can then be placed in contact with the protective layer to form a seal.

Once the protective layer 674 has been placed around the wound 690, an integrated contact layer and sealant layer 602 connected to a suction apparatus 604 of a reduced pressure tissue therapy device 600 is placed over the first protective layer 674 as shown in FIG. 6. An airtight seal is formed between the integrated contact layer and sealant layer 602 and the protective layer 674. In such an embodiment, the protective layer 674 may be left in place and the integrated contact layer and sealant layer 602 changed approximately every three (3) to seven (7) days. In some embodiments, the integrated contact layer and sealant layer 602 is changed about every four (4) days. In some embodiments, the integrated contact layer and sealant layer 602 is changed about every five (5) days. In some embodiments, the integrated contact layer and sealant layer 602 is changed about every six (6) days. In some embodiments, the integrated contact layer and sealant layer 602 is changed about every seven (7) days. In some embodiments, only a sealant layer is placed in contact with the protective layer. The protective layer in such an embodiment may be changed if there is a loss of adhesion between the protective layer and the skin of the patient. In some embodiments, the protective layer may be changed if the wound edges have migrated enough to warrant adjusting the protective layer to accommodate the changed size of the wound.

Figure 12:
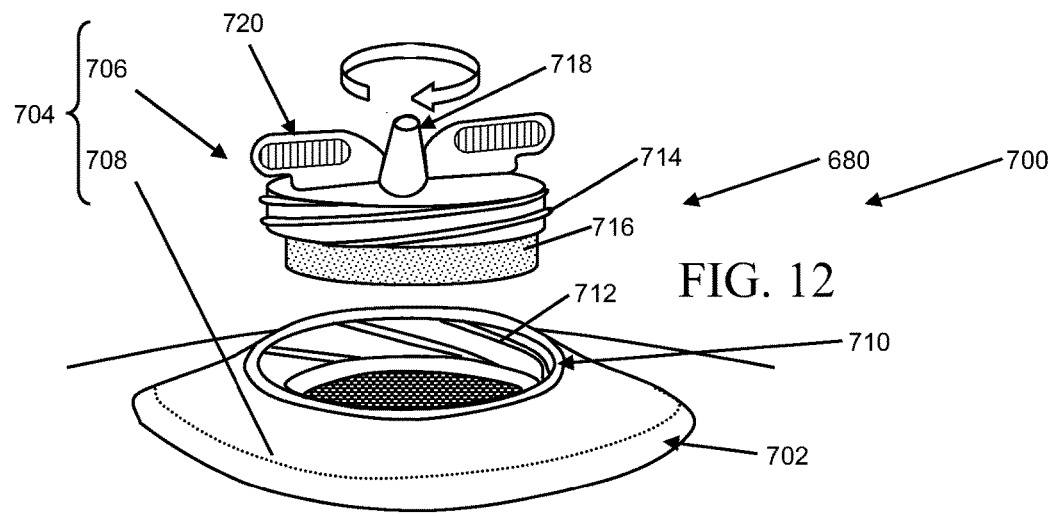
FIG. 12 is a perspective view of another embodiment of a sealant layer in which a sealing base is affixed to the patient's skin and a sealing cap is than screwed into the sealing base thereby creating an easily removable sealant layer.

FIG. 12 depicts another embodiment of a tissue therapy device 700, comprising a sealing layer 702 with a resealable interface 704. In some embodiments, the resealable interface 704 may permit access to the tissue underneath the sealing layer 702, without requiring replacement of the sealing layer 702, or compromising the seal between the sealing layer 702 and the patient's skin. This may be beneficial, for example, for inspecting the treatment area, changing the contact layer, debriding a wound, and/or to applying any topical agents. In the particular embodiment depicted in FIG. 12, the resealable interface 704 comprises a cap member 706 and a base member 708 attached to the sealing layer 702. The base member 708 comprises a resealable aperture 710 that is configured to form a complementary interfit with the cap member 706. In this particular embodiment, the resealable aperture 710 and the cap member 706 comprises complementary threads 712 and 714, respectively. In other embodiments, however, a snapfit or a latch may be provided to secure the cap member 706 to the base member 708. In some embodiments, hinge or flexible elongate member may be provided to keep the cap member 706 attached to the base member 708. In some embodiments, one or more gaskets may be provided on cap member 706 and/or the base member 708 to facilitate an airtight seal. In some embodiments, as shown in FIG. 12, a contact layer 716 may be integrally formed with the cap member 706, such that when changing the contact layer 716, the cap member 706 is removed from the base member 708 and replaced with a new cap member 706 with contact layer 708. In the embodiment illustrated in FIG. 12, a suction aperture 718 is provided on the cap member 706 for attachment to a suction apparatus, but in other embodiments, the suction aperture may also be provided on the base member. In some embodiments, multiple suction apertures may be provided. The cap member 706 may optionally comprise one or more tab members 720 or other structures to facilitate opening and closing of the cap member 706. The base member 708 may also optionally comprise a tab member or other structure to stabilize the base member 708 while manipulating the cap member 706, which may reduce the risk of compromising the seal between the patient and the sealing layer 702.

Figure 7A:
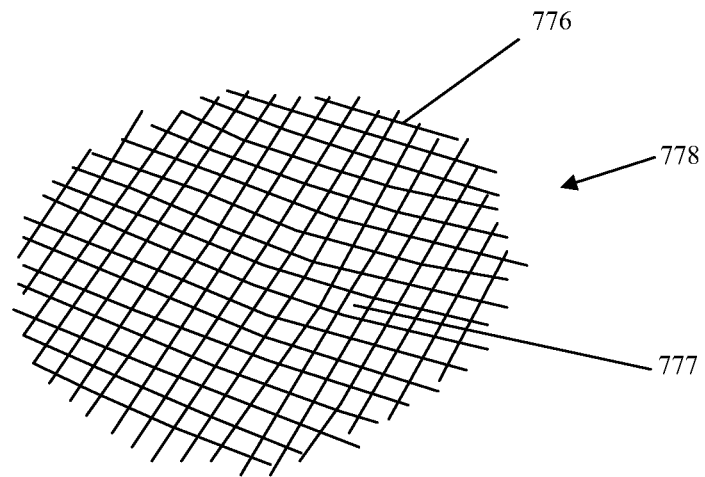
FIG. 7A depicts one embodiment of a single layer of a stacked mesh matrix that may be used as a contact layer.
Figure 7B:
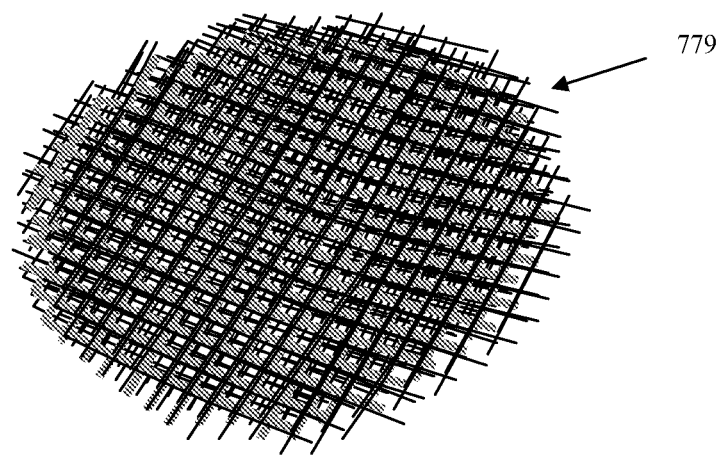
FIG. 7B shows multiple sheets of mesh matrix stacked together to form a stacked mesh matrix.

In some embodiments, the contact layer of the wound dressing comprises a stacked mesh matrix. The stacked mesh matrix is shown in FIGS. 7A and 7B. The stacked mesh matrix comprises one or more mesh matrix sheets 778 of thin filaments 776 as shown in FIG. 7A. In some embodiments, the filaments are between approximately 0.001 mm to approximately 10 mm thick. In some embodiments, the filaments are more than approximately 0.01 mm thick. In some embodiments the filaments are more than approximately 0.05 mm thick. In some embodiments, the filaments are more than approximately 0.1 mm thick. In some embodiments the filaments are more than approximately 0.5 mm thick. In some embodiments, the filaments are more than approximately 1 mm thick. In some embodiments the filaments are more than approximately 2.5 mm thick. In some embodiments, the filaments are approximately more 5 mm thick. In some embodiments, the filaments are approximately more than 7.5 mm thick. In some embodiments, the filaments are approximately more than 10 mm thick. In some embodiments, the filaments are less than approximately 10 mm thick. In some embodiments, the filaments are less than approximately 5 mm thick. In some embodiments the filaments are less than approximately 1 mm thick. In some embodiments, the filaments are less than approximately 0.05 mm thick. In some embodiments the filaments are less than approximately 0.01 mm thick. In some embodiments the filaments are less than approximately 0.005 mm thick. In some embodiments, the filaments are less than 0.001 mm thick. In some embodiments, the filaments throughout the stacked mesh matrix are of a uniform thickness. In other embodiments, the filament thickness is variable throughout the stacked mesh matrix. The filaments may be made of any suitable biocompatible material known in the art, such as polymer. In some aspects, the filaments 776 are less than 10 mm thick. In some aspects, the filaments are approximately 0.001 mm to approximately 10 mm thick. In some embodiments, the filaments within a single mesh matrix sheet 778 have the same uniform thickness. In some embodiments, the filaments within a single mesh sheet 778 have variable thickness within the sheet.

The filaments 776 of the mesh matrix sheet 778 may be oriented such that they lie perpendicular in orientation to one another, or at some other angle. In other embodiments, the filaments may be oriented randomly within the sheet. In some embodiments of the wound therapy device, the stacked mesh matrix comprises mesh matrix sheets where the filaments of the mesh matrix sheet are spaced between approximately 1 mm to 15 mm apart. In some embodiments the filaments are spaced more than about 1 mm apart. In some embodiments the filaments are spaced more than about 2 mm apart. In some embodiments the filaments are spaced about 4 mm apart. In some embodiments the filaments are spaced about 6 mm apart. In some embodiments the filaments are spaced about 8 mm apart. In some embodiments the filaments are space about 10 mm apart. In some embodiments the filaments are spaced about 12 mm apart. In some embodiments the filaments are spaced about 15 mm apart. In other embodiments the filaments are spaced between approximately 1 mm to approximately 5 mm. In some embodiments the filaments are spaced between approximately 5 mm to 10 mm apart. In some embodiments the filaments 776 are spaced approximately 10 mm to 15 mm apart. In some embodiments, the filaments 776 are spaced uniformly throughout the mesh matrix sheet 778. In some embodiments, the filaments 776 are variably spaced throughout the mesh matrix sheet. In some aspects, the spacing between filaments is variable. In some aspects the filaments 776 may be hollow.

Each of the mesh structures may have a uniform or a non-uniform size, shape or configuration with respect to the other mesh structures. In some embodiments, one or more sheets may have a generally planar configuration, but in other embodiments, one or more sheets may have a non-planar configuration. In some embodiments, the edges of a mesh sheet may comprise the ends of the tubes that comprise the mesh sheet. In other embodiments, the mesh sheet may be configured with an annular edge comprising one or more tubes. In some embodiments, the annular edge may reduce the degree of tissue response to the mesh sheet compared to an edge comprising tube ends.

In some embodiments, the mesh sheet may be rigid, semi-rigid, or flexible. In some embodiments, the degree of flexibility may vary depending upon the degree of hydration of the mesh sheet. In embodiments, the degree of flexibility may be isotropic or anisotropic. In some embodiments, one or more mesh sheets may have a generally planar configuration, while in other embodiments, one or more mesh sheets may have a curved, corrugated, egg-crated shape, or other non-planar configuration. In some embodiments, the mesh matrix may comprise be arranged so that the configurations or orientations of adjacent mesh sheets are non-uniform. In embodiments where the mesh sheets are non-planar, small spaces may be formed between the adjacent mesh sheets. Depending upon the type of material comprising the mesh sheets, in some embodiments, the sheets may be adherent or non-adherent to each other with contact.

The filaments comprising a mesh sheet may be configured to have a length extending from one edge of a sheet to another edge of the sheet. In other embodiments, one or more filaments may have a length and orientation where the filaments ends are not located at an edge of the sheet. The filaments may have any of a variety of cross-sectional shapes, including but not limited to circles, ovals, squares, rectangles, triangles or any other polygonal or closed-ended shape. The cross-sectional shape or cross-sectional area of a filament need not be uniform along its longitudinal length. In some embodiments, a mesh sheet may further comprise a non-tubular or non-elongate structure, such as a disc or a cube. The non-tubular structures may comprise the same or a different material.

In some embodiments, one or mesh sheets may comprise one or more biodegradable or bioabsorbable materials. In some embodiments, the biodegradable materials may be metallic or non-metallic, including but not limited to biodegradable polymers. Examples of such polymers include but are not limited to various forms of polycaprolactone, poly (L-lactide)s, poly(DL-lactide)s, polyglycolide, poly(L-lactide-co-D, L-ILactide), Poly (DL-lactide-co-glycolide), poly(DL-lactide-co-caprolactone), polydioxanone, polyesteramide, copolyoxalate, poly (glutamic-co-leucine), and combinations thereof.

In addition to the spacing and size of the openings provided by the arrangement of the substructures that comprise a mesh sheet, the substructures themselves may also have a surface porosity. The pores may substantially uniform or non-uniform in size, shape and/or configuration. In some embodiments, the average surface porosity of a tube, for example, may be about 1 nm to about 500 µm or more, sometimes about 5 nm to about 100 µm, and other times about 50 nm to about 500 nm.

Figure 10A:
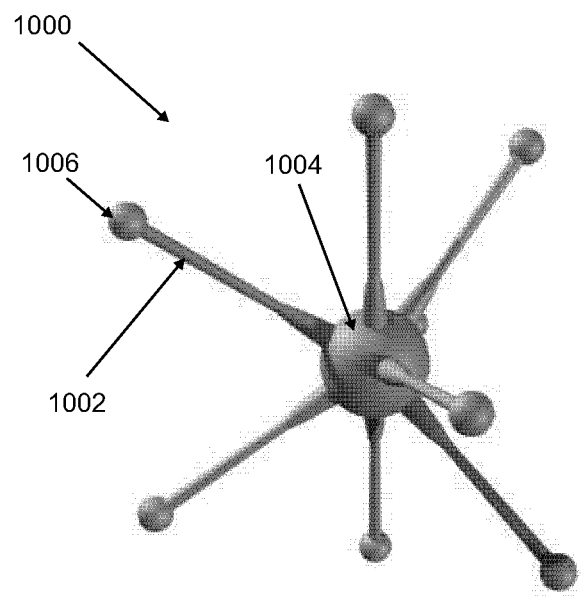
FIG. 10A depicts another embodiment of a contact layer structure.
Figure 10B:
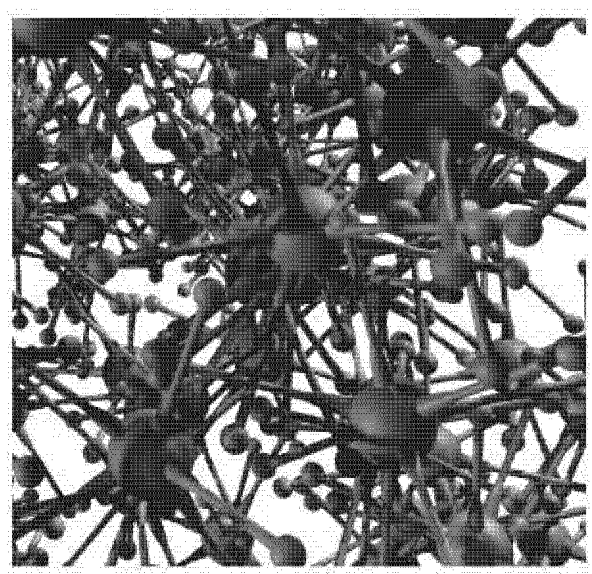
FIG. 10B schematically depicts one example of the aggregation of the contact layer structure in FIG. 10A.

In addition to mesh sheets and layered mesh matrices, in other embodiments, the contact layer may comprise one or more non-sheet structures. In some embodiments, the contact layer may comprise a plurality of small, loose structures or particles that may have a generally two-dimensional or three-dimensional configuration. In some embodiments the non sheet structures may be packed into a porous pouch so as to enables easy placement and replacement of the non sheet structures from the damaged tissue cavity. These non-sheet structures may be used with or without mesh sheets. In some embodiments, the non-sheet structures may have any of a variety shapes, including but not limited to filaments, chips, ball, cube, conical, frusto-conical or pyramidal shapes, for example. Some of the shapes may have a complex, three-dimensional configuration. In FIG. 10A, for example, the non-sheet structure or particle 1000 may comprise a plurality of appendages or tubes 1002 have one or more convergent sites 1004. In some embodiments, the tubes 1000 have any of a variety of features as described for the tubes comprising the mesh sheets. FIG. 10B depicts one embodiment of the aggregation of a plurality of particle 1000. In this particular example, the overall structure comprises a porous, three-dimensional matrix which should be preferably packed into a porous pouch. In some embodiments, each of the particles may have an overall average dimension of about 0.5 mm to about 20 mm, sometimes about 5 mm to about 15 mm, and other times about 3 mm to about 7 mm. The aggregate porosity of the matrix formed may vary, depending on the length and thickness of the tubes 1002. The length and thickness of tubes 1002 may be uniform or non-uniform on the same particle or between different particles. The tubes 1002 depicted in FIG. 10A comprise ball-shaped end structures 1006, but in other embodiments, end structures of other shapes may be provided, or end structures may be omitted on one or more tubes 1002. In some embodiments, particles 1000 may be pre-hydrated outside the wound or tissue treatment area and allowed to adhere to each other. The three-dimensional matrix formed by the particles may be pre-shaped prior to placement at the tissue treatment site, or packed into a porous pouch. Other pouch-based embodiments are described in greater detail below.

In some embodiments, the stacked mesh matrix 779 comprises at least two mesh matrix sheets 778. In some embodiments, the stacked mesh matrix 779 will comprises two mesh matrix sheets 778 of FIG. 7A. In an alternate embodiment, the wound dressing comprises multiple mesh matrix sheets 778 as shown in FIG. 7B. In some embodiments, the individual mesh matrix sheets that are stacked together to form a stacked mesh matrix have the same filament thickness and the same filament spacing as the other mesh matrix sheets comprising the stacked mesh matrix. In some embodiments, the individual mesh matrix sheets that are stacked together to form a stacked mesh matrix have different filament thickness and different filament spacing as compared to the other mesh matrix sheets comprising the stacked mesh matrix. The single sheets 778 are adhered together to form the stack mesh matrix 779, but can be peeled apart so that the height of the dressing can be adjusted to the depth of the wound. The size of the communicating pathways 777 depends on the stack depth and filament spacing and can be configured to different sizes depending on the drainage needs of the wound.

Figure 8:
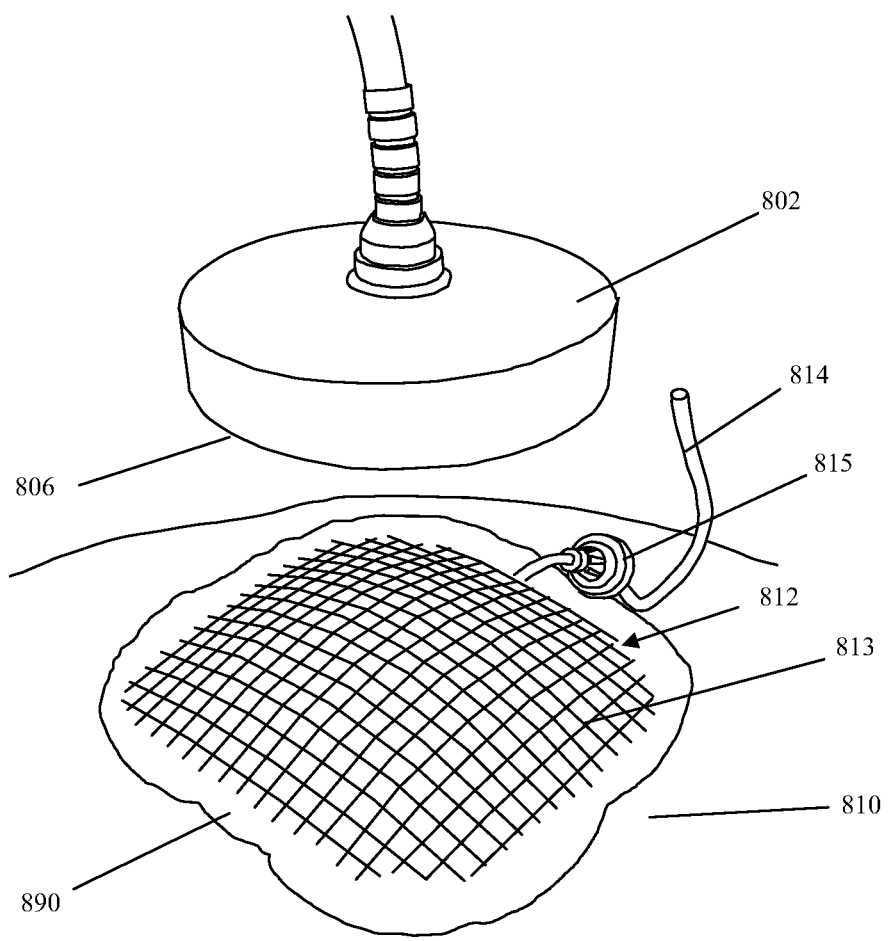
FIG. 8 is one embodiment of a top side view of an illustration of a reduced pressure tissue therapy device comprising a wound dressing with a flexible neck positioned to be placed over a stacked mesh matrix further comprising a delivery mesh.

In some embodiments, the reduced pressure tissue therapy device may include a delivery mesh to provide variable-pressure assisted irrigation or delivery of biologics to the wound. In some embodiments, the delivery mesh comprises filaments that are soaked with the solution to be delivered. In such an embodiment, the solution diffuses into the wound area from the filaments. In some embodiments, the reduced pressure tissue therapy device comprises a network of interconnected hollow tubes 813 arranged in a mesh-like configuration to form a delivery mesh 812, as seen in FIG. 8. The delivery mesh 812 is placed over the wound 890. In one embodiment, the delivery mesh is sealed underneath the sealant layer 802 of the wound dressing of the reduced pressure tissue therapy device. In such an embodiment, the network of hollow tubes 813 may be perfused with a solution. In one aspect, the solution contains antibiotics. In another aspect, the solution contains biologics, such as growth factors. In some embodiments, the delivery mesh 812 described herein may be used to irrigate the wound. In some embodiments, the delivery mesh 812 described herein may be used with a reduced pressure tissue therapy device. In one embodiment, the delivery mesh 812 is sized and placed on the wound 890 of a patient 810. The delivery mesh 812 incorporates a supply tube 814 with a supply tube connector 815 at the end of the supply tube 814. The supply tube 814 is connected to a fluid supply reservoir through the supply tube connector 815. The supply tube 814 may be connected to the fluid supply reservoir by snapping the connector together. Alternatively, the supply tube and the fluid supply reservoir may be connected by screwing the connector together. Once the delivery mesh 812 is placed over the wound 890, the sealant layer 802 of the wound dressing of a reduced pressure tissue therapy device may be placed over the delivery mesh 812. The contact surface 806 of the wound dressing is in fluid communication with the delivery mesh and is placed over the delivery mesh 812 to apply reduced pressure to the wound surface.

Figure 9A:
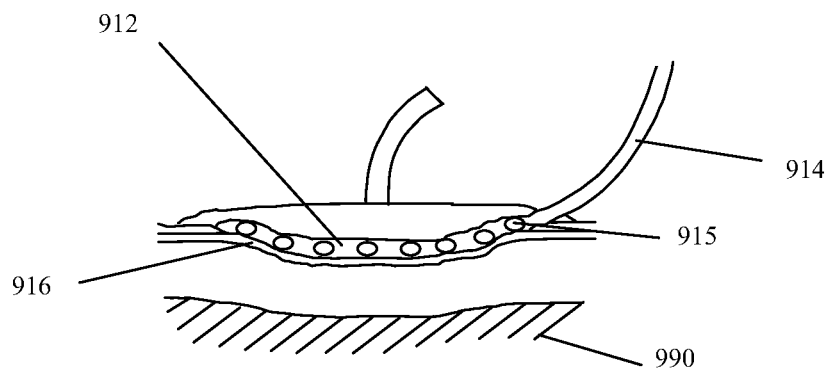
FIGS. 9A to 9C depict one embodiment of a method of using delivery mesh together with a reduced pressure tissue therapy device.
Figure 9B:
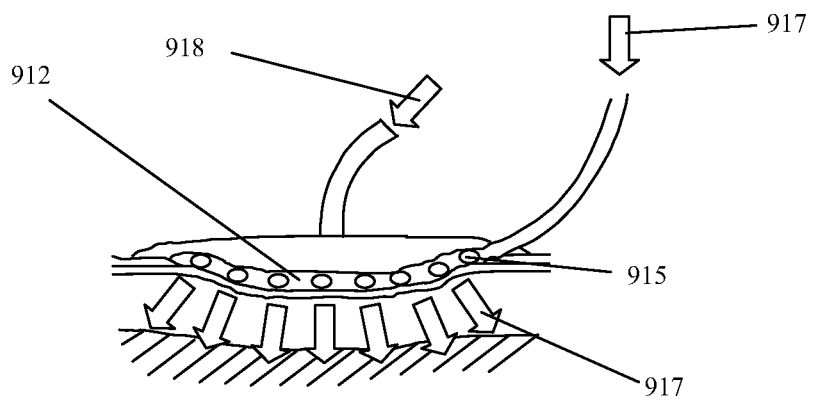

Provided herein is a delivery mesh for the delivery of biologics or antibiotics to the wound. In such an embodiment, a solution containing biologics or antibiotics, or a solution suitable for delivery to a wound, may be delivered to the wound 990 from a fluid reservoir through a supply tube 914. The solution may be delivered to the wound through perforations 915 on the underside 916 of the delivery mesh 912 as seen in FIG. 9A. As seen in FIG. 9B, the perforations 915 provide fluid communication between the delivery mesh 912 and the wound 990. In some embodiments, the delivery mesh 912 may be constructed into predetermined sizes where the size of the delivery mesh used depends on the size of the wound. In some embodiments, the delivery mesh may be constructed such that the edges may be trimmed such that the delivery mesh is and adequate size for the wound surface. In some embodiments, such a delivery mesh comprises hollow filaments. In a further embodiment of a delivery mesh comprising hollow filaments, the delivery mesh may be trimmed and the hollow filaments may self-seal in the places where the delivery mesh is cut, such that fluid will not leak out of the ends. In an alternate embodiment, the hollow filaments of the delivery mesh will not self-seal when cut. In such an embodiment, solution will be able to reach the wound through the edges of the delivery mesh.

Figure 9C:
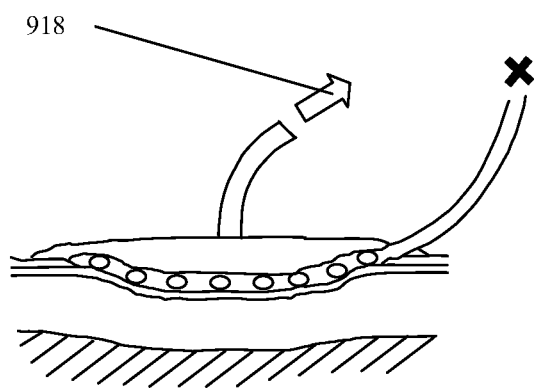

In one embodiment of the reduced pressure tissue therapy device, the device and delivery mesh may be used in conjunction with a mechanical pump. In such an embodiment, the pump can deliver normal therapeutic reduced pressure, but may also be used to deliver positive therapeutic pressure to enhance distribution of solution to the wound. In such an embodiment, the delivery mesh 912 of FIG. 9A may be connected to an external infusion pump. In one embodiment, when a solution is being delivered by the infusion pump through an infusion tube 917, the mechanical pump of the reduced pressure tissue therapy device could be set to apply positive pressure to the wound surface through a pressure delivery tube 918 in order to facilitate the delivery of the solution to the wound, as shown in FIG. 9B. After the infusion of solution through the infusion tube 917 is stopped (represented by X in FIG. 9C), the mechanical pump of the reduced pressure tissue therapy device can then be reversed so that reduced pressure is applied to the wound through the pressure delivery tube 918 (FIG. 9C). In an alternate embodiment, the infusion solution may be void of biologics and may serve to irrigate the wound and mobilize particles which the negative pressure could then remove from the wound bed. Additionally, the delivery mesh may be designed such that the space between the filaments of the mesh would also serve as an area which supports wound in-growth.

In another alternate embodiment, a sealed and evacuated bottle may be used as a vacuum source. In some embodiments, the bottle may comprise a screw-in connector. The receptacle for the bottle on the dressing may comprise a mechanism or structure to break a seal on the bottle when the bottle is connected, thereby applying the negative pressure from the bottle to the wound or tissue treatment site.

In some embodiments, the particles may be placed or packed into one or more porous pouches, which may be placed into a tissue cavity. The particles may be loosely packed, permitting substantial movement of particles within the pouch, or tightly packed, where significant particle movement is limited due to particle density. Typically, the porosity of the pouch is smaller than the average size of the particles, but in other embodiments, the porosity of the pouch may be greater. In some embodiments, one or more tubular structures may project out from the pores of the pouch but the particles do not separate from the pouch. In still other embodiments, the pouch is configured such that the particles or other components within the pouch may be released over time.

Figure 14A:
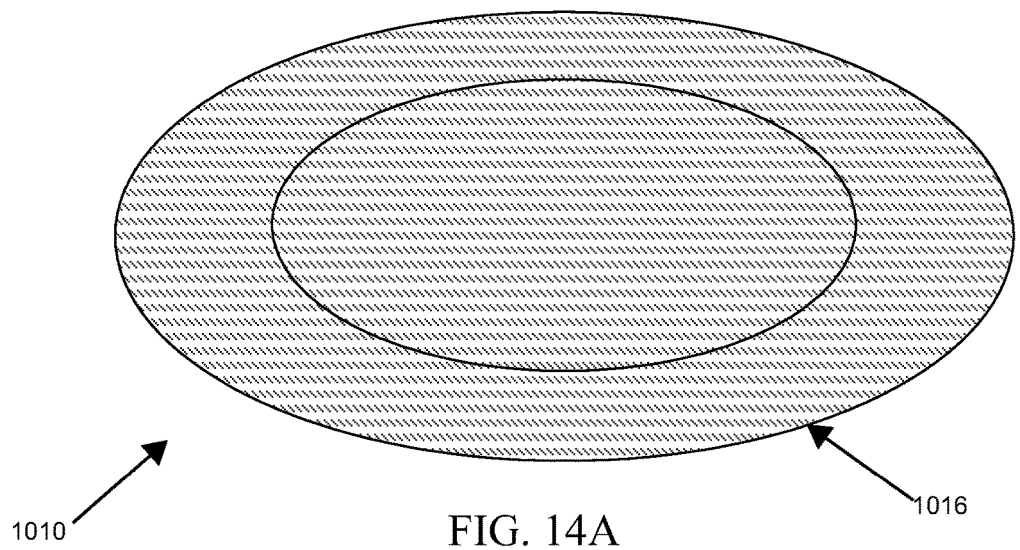
FIGS. 14A and 14B are top elevational and cross-sectional views of a pouch containing a plurality of cover layer structures.
Figure 14B:
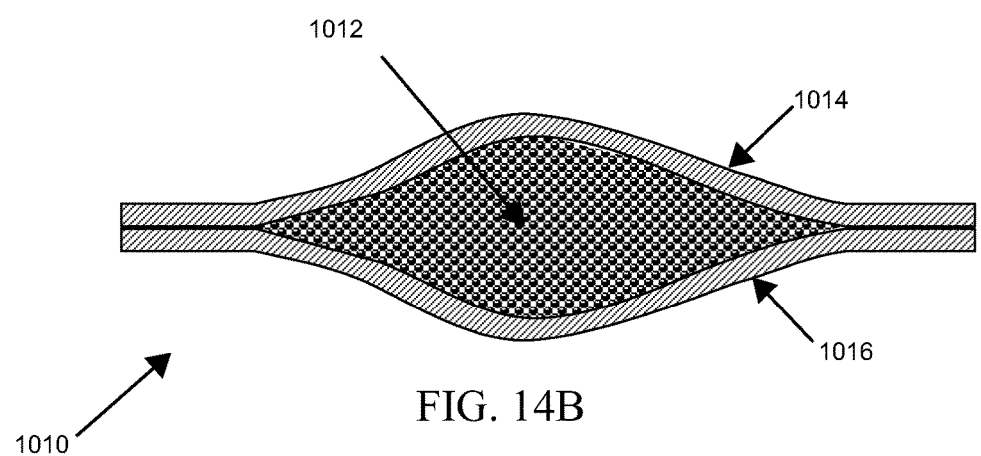
Figure 15:
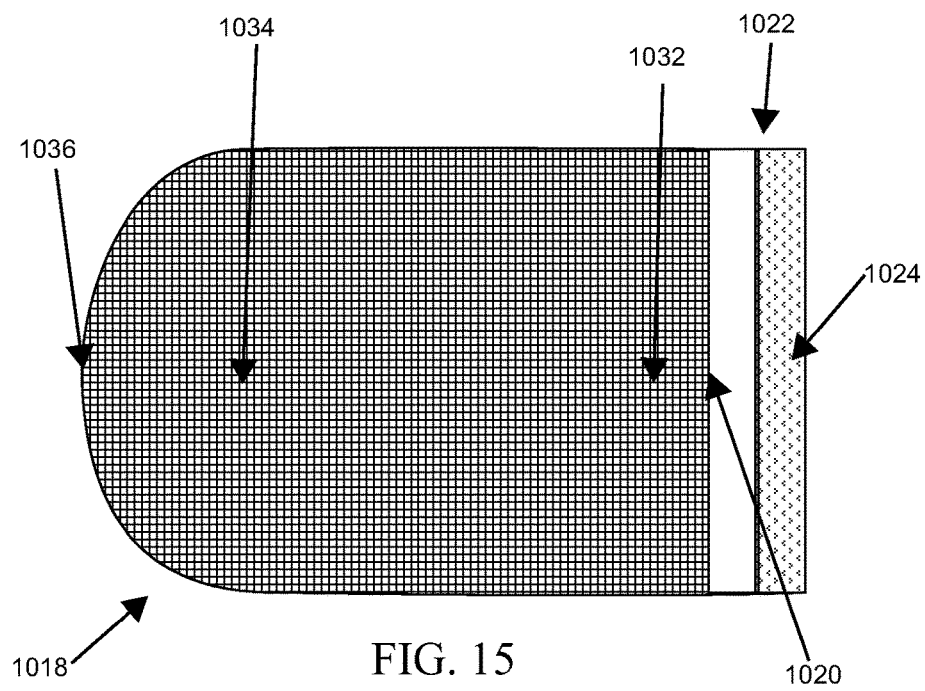
FIG. 15 is top elevational view of another embodiment of a pouch.
Figure 16:
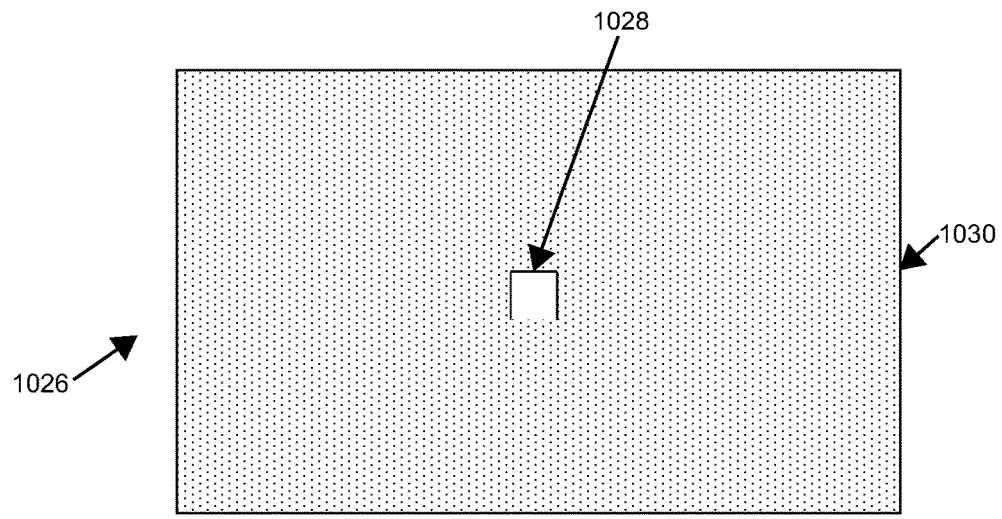
FIG. 16 is a top elevational view of still another embodiment of a pouch.

In some embodiments, the pouches are filled and sealed at the point-of-manufacture, while in other embodiments, the pouches are filled at the point-of-use. FIGS. 14A and 14B depict one embodiment of a pouch 1010 with a circular configuration and comprising a plurality of particles 1012 or structures. The pouch 1010 is filled and sealed at the point of manufacture and is not configured to be reopened. In this particular embodiment, the pouch 1010 comprises two layers of edge-sealed porous materials 1014, 1016, but in other embodiments, may comprise a single layer of porous material folded onto itself and sealed against itself. The two layers of porous materials need not comprise the same material or have the same porosity characteristics. In FIG. 15, a mesh pouch 1018 is provided with a sealable opening 1020. In some embodiments, upon sealing of the sealable opening 1020, the opening is not configured to be reopened without damaging the pouch. In other embodiments, the sealable opening 1020 is a resealable opening 1020, and may be reopened and may be emptied, refilled or topped off with particles or structures. In this particular embodiment, the sealable opening 1020 comprises a flap 1022 with an adhesive 1024, but in other embodiments, any of a variety of sealable or resealable openings may be provided, including but not limited to a heat sealable flap opening, a pursestring opening, a zipper-type opening, a snap-fit opening, a hook-and-loop type of opening, etc. The pouch 1018 may be pre-filled at the point-of-manufacture with the particles or may be empty. In some embodiments, the pouches may have any of a variety of shapes, including but not limited to circles, tapered discs, balls, ovals, ovules, rectangles, squares, boxes, and the like. In some embodiments, the pouch may have an adjustable shape. Although the pouch 1026 depicted in FIG. 15 comprises a sealable opening 1028 located at an edge of the pouch, in other embodiments, such as the pouch 1026 depicted in FIG. 16, the pouch 1026 comprises an opening 1028 that is located away from the pouch edge 1030. In this particular embodiment, the opening 1028 comprises a duck bill valve in which a syringe or other elongate member may be inserted to add or remove cover layer structures.

In some embodiments, the pouch may be filled with a variable amount of particles or contact layer structures. In some embodiments, the structure of the pouch may be adjusted to different fill volumes. For example, the pouch 1018 depicted in FIG. 15 may be sealed at one location 1032 if substantially full, or may folded and sealed at a second location 1034 if filled with a substantially smaller volume. In some instances, the flap 1022 may be folded over the distal end 1036 of the pouch 1018 and sealed on the other side of the pouch 1018.

While various embodiments have been described and presented herein, those embodiments are provided by way of example only. Variations, changes and substitutions may be made without departing from the invention. It should be noted that various alternatives to the exemplary embodiments described herein may be employed in practicing the invention. For all of the embodiments described herein, the steps of the methods need not be performed sequentially.

What is claimed as new and desired to be protected by Letters Patent of the United States is:

1. A reduced pressure therapy system, the system comprising:
    a wound dressing comprising:
        a sealing film comprising an adhesive region, wherein the sealing film is configured to be affixed around an area of tissue to be treated and create a sealed enclosure,
        an outlet port, and
        a contact layer comprising a plurality of stacked sheets retained by a porous layer;
    a suction apparatus configured to generate reduced pressure of at least −50 mm Hg, the suction apparatus comprising:
        a first chamber having a distal end and a proximal end, wherein the first chamber has rigid sides having first threads from the distal end to the proximal end of the first chamber on an internal surface,
        a reciprocating member comprising second threads on an outer surface configured to engage the first threads to form a threaded interface allowing the reciprocating member to sealably rotate along the rigid sides,
        a second chamber, and
        a valve controlling fluid communication with the second chamber; and
    an extension tube configured to attach to the outlet port of the wound dressing and to the suction apparatus.

2. The system of claim 1, further comprising a protective layer configured to be applied to the area of tissue before the wound dressing is applied.

3. The system of claim 1, further comprising a hydrocolloid configured to be applied to the area of tissue.

4. A reduced pressure therapy system, the system comprising:
    a wound dressing comprising a contact layer that includes a plurality of stacked sheets retained by a porous layer;
    a portable suction apparatus configured to generate reduced pressure of at least −50 mm Hg, the portable suction apparatus comprising:
        a first chamber having a distal end and a proximal end, wherein the first chamber has rigid sides having first threads from the distal end to the proximal end of the first chamber on an internal surface,
        a rotatable sealing member configured to sealably rotate along the rigid sides, wherein the rotatable sealing member comprises second threads that engage the first threads,
        a second chamber, and
        a valve configured to control fluid communication with the second chamber; and
    an extension tube configured to attach to an outlet port of the wound dressing and to the portable suction apparatus.

5. The system of claim 1, wherein an interior of the extension tube is in communication between the outlet port and the suction apparatus.

6. The system of claim 4, wherein the valve is a three-way valve.

7. The system of claim 4, wherein the rotatable sealing member is configured to sealingly rotate along the rigid sides in an opposite direction from a direction of insertion of the rotatable sealing member within the first chamber.

8. The system of claim 4, wherein the first chamber is configured to receive exudate from the wound dressing.

* * * * *